US006970792B1

(12) United States Patent
Diab

(10) Patent No.: US 6,970,792 B1
(45) Date of Patent: Nov. 29, 2005

(54) SYSTEMS AND METHODS FOR DETERMINING BLOOD OXYGEN SATURATION VALUES USING COMPLEX NUMBER ENCODING

(75) Inventor: Mohamed K. Diab, Mission Viejo, CA (US)

(73) Assignee: Masimo Laboratories, Inc., Irvine, CA (US)

( * ) Notice: Subject to any disclaimer, the term of this patent is extended or adjusted under 35 U.S.C. 154(b) by 32 days.

(21) Appl. No.: 10/727,348

(22) Filed: Dec. 3, 2003

Related U.S. Application Data

(60) Provisional application No. 60/430,834, filed on Dec. 4, 2002.

(51) Int. Cl.[7] .......................... G06F 19/00; A61B 5/00
(52) U.S. Cl. ........................ 702/32; 702/189; 702/190; 600/323; 600/515
(58) Field of Search ............................ 702/30, 31, 32, 702/189, 190, 198; 600/323, 324, 336, 515–519

(56) References Cited

U.S. PATENT DOCUMENTS

| | | | |
|---|---|---|---|
| 5,337,744 A | 8/1994 | Branigan | |
| 5,452,717 A | 9/1995 | Branigan et al. | |
| 5,482,036 A | 1/1996 | Diab et al. | |
| 5,490,505 A | 2/1996 | Diab et al. | |
| 5,553,615 A * | 9/1996 | Carim et al. ................ | 600/324 |
| 5,632,272 A | 5/1997 | Diab et al. | |
| 5,638,816 A | 6/1997 | Kiani-Azarbayjany et al. | |
| 5,638,818 A | 6/1997 | Diab et al. | |
| 5,645,440 A | 7/1997 | Tobler et al. | |
| 5,685,299 A | 11/1997 | Diab et al. | |
| D393,830 S | 4/1998 | Tobler et al. | |
| 5,743,262 A | 4/1998 | Lepper, Jr. et al. | |
| 5,758,644 A | 6/1998 | Diab et al. | |
| 5,760,910 A | 6/1998 | Lepper, Jr. et al. | |
| 5,769,785 A | 6/1998 | Diab et al. | |
| 5,782,757 A | 7/1998 | Diab et al. | |
| 5,823,950 A | 10/1998 | Diab et al. | |
| 5,860,919 A | 1/1999 | Kiani-Azarbayjany et al. | |
| 5,890,929 A | 4/1999 | Mills et al. | |
| 5,919,134 A | 7/1999 | Diab | |
| 5,934,925 A | 8/1999 | Tobler et al. | |
| 5,940,182 A | 8/1999 | Lepper, Jr. et al. | |
| 5,995,855 A | 11/1999 | Kiani et al. | |
| 5,997,343 A | 12/1999 | Mills et al. | |
| 6,002,952 A | 12/1999 | Diab et al. | |
| 6,011,986 A | 1/2000 | Diab et al. | |
| 6,036,642 A | 3/2000 | Diab et al. | |
| 6,067,462 A | 5/2000 | Diab et al. | |
| 6,081,735 A | 6/2000 | Diab et al. | |
| 6,088,607 A | 7/2000 | Diab et al. | |
| 6,110,522 A | 8/2000 | Lepper, Jr. et al. | |
| 6,151,516 A | 11/2000 | Kiani-Azarbayjany et al. | |
| 6,152,754 A | 11/2000 | Gerhardt et al. | |

(Continued)

OTHER PUBLICATIONS

Wukitsch, M.W., BA,, et al. Pulse Oximetry: Analysis of Theory, Technology, and Practice, Journal of Clinical Monitoring, vol. 4, (1988). pp. 290-301.

*Primary Examiner*—Bryan Bui
(74) *Attorney, Agent, or Firm*—Knobbe, Martens, Olson & Bear, LLP

(57) ABSTRACT

The disclosure includes pulse oximetry systems and methods for determining point-by-point saturation values by encoding photoplethysmographs in the complex domain and processing the complex signals. The systems filter motion artifacts and other noise using a variety of techniques, including statistical analysis such as correlation, or phase filtering.

17 Claims, 22 Drawing Sheets

U.S. PATENT DOCUMENTS

| | | |
|---|---|---|
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 2003/0073890 A1 * | 4/2003 | Hanna ........................ 600/323 |

* cited by examiner

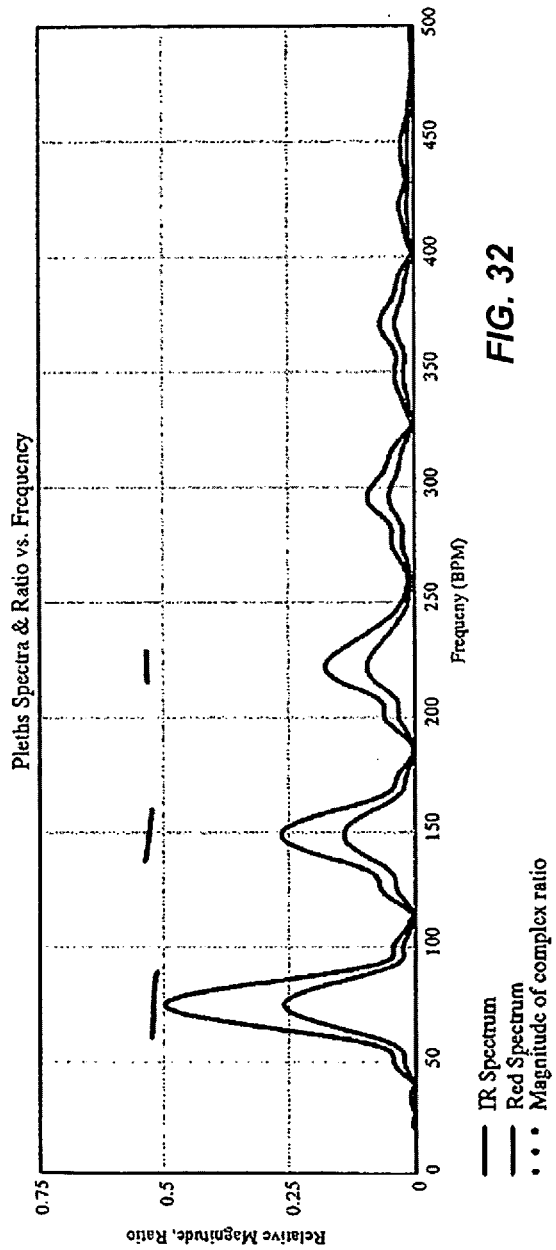
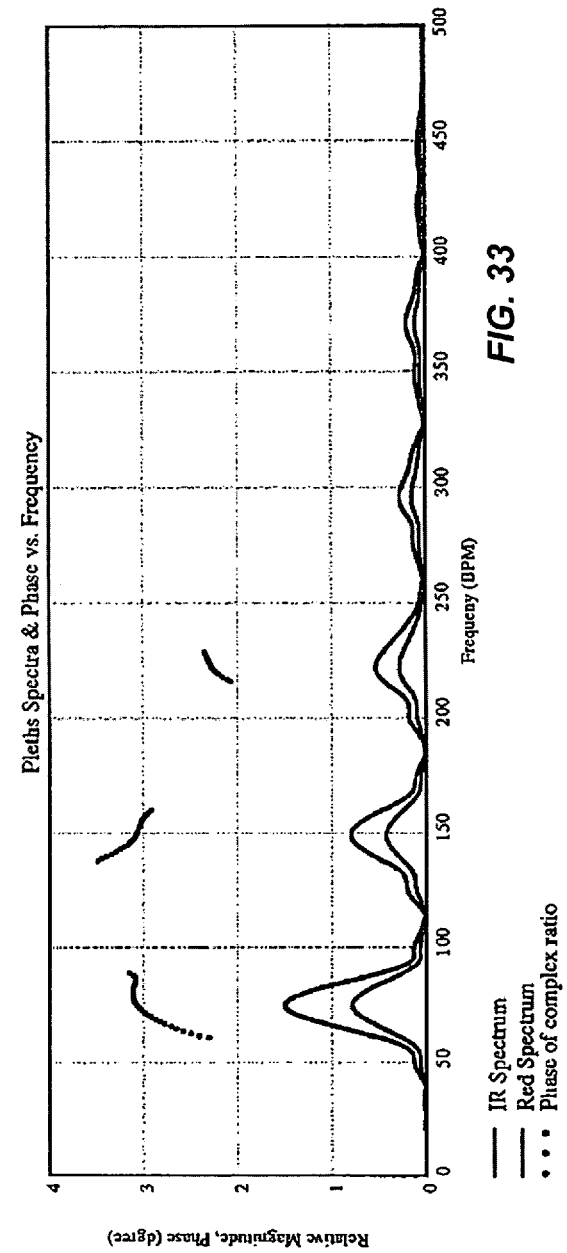

SYSTEMS AND METHODS FOR DETERMINING BLOOD OXYGEN SATURATION VALUES USING COMPLEX NUMBER ENCODING

REFERENCE TO RELATED APPLICATIONS

The present application claims priority benefit under 35 U.S.C. §119(e) from U.S. Provisional Application No. 60/430,834, filed Dec. 4, 2002, entitled, "Systems and Methods for Determining Blood Oxygen Saturation Values Using Complex Number Encoding," which is incorporated herein by reference.

FIELD OF THE INVENTION

The present invention relates to the field of pulse photometery. More specifically, the invention relates to calculating continuous saturation values using complex number analysis.

BACKGROUND OF THE INVENTION

Pulse photometry is a noninvasive technique for measuring blood analytes in living tissue. In this technique, multiple light sources emit light of differing wavelengths, which is transmitted through or reflected from a vascular bed. One or more photodetectors then detect the transmitted or reflected light as an optical signal. As the photons propagate through the tissue, they are subjected to random absorption and scattering processes due to the nonhomogeneous nature of the tissue. These effects manifest themselves as a loss of energy in the optical signal, and are generally referred to as bulk loss. In addition to bulk loss, the optical signal is modulated by the flow of arterial blood into the vascular bed. Moreover, the movement of venous blood into or out of the tissue, local tissue compression and local muscle movements super-impose yet another modulation on the optical signal, usually of lower frequency than the arterial flow. For example, FIG. 1 illustrates detected optical signals that include the foregoing attenuation, arterial flow modulation, and low frequency modulation. Each optical signal, with its combined attenuation and modulations, e.g., each combined optical signal, is generally referred to as a photoplethysmograph (photopleth.)

Pulse oximetry is a special case of pulse photometry where the oxygenation of arterial blood is sought in order to estimate the state of oxygen exchange in the body. In order to calculate the oxygen saturation of arterial blood, two wavelengths of light, e.g. Red, at about 660 nm, and Infrared, at about 900 nm, are used to calculate the ratio of two dominant hemoglobin components, oxygenated hemoglobin ($HBO_2$) and deoxygenated hemoglobin (HB). The detected optical signals, which correspond to the Red and Infrared wavelengths, are first normalized in order to balance the effects of unknown source intensity as well as unknown bulk loss at each wavelength. The arterial pulses are then isolated by filtering each normalized signal, where a high pass or a band-pass filter takes advantage of the typically higher frequency of the pulsatile arterial blood, hence the name pulse oximetry. This normalized and filtered signal is referred to as the AC component and is typically sampled with the help of an analog to digital converter with a rate of about 30 to about 100 samples/second. For example, FIG. 2 illustrates the optical signals of FIG. 1 after they have been normalized and bandpassed.

In order to estimate blood oxygenation, a (Red/Infrared) ratio is calculated by dividing the strength of the Red AC (RdAC) by the corresponding strength of the Infrared AC (IrAC). The (RdAC/IrAC) ratio is then generally plugged into an empirical calibration curve equation that relates it to blood oxygenation. For example, reference can be made to Japanese Patent No. Sho 50/1975-128387, issued to Aoyagi, entitled "Optical Type Blood Measuring Equipment."

The arterial blood flow generally has a higher fundamental frequency than other components of the photopleth, however, there are cases where the two frequencies may overlap. One such example is the effect of motion artifacts on the optical signal, which is described in detail in U.S. Pat. No. 6,157,850, issued to Diab et al., entitled "Signal Processing Apparatus." Another effect occurs whenever the venous component of the blood is strongly coupled, mechanically, with the arterial component. This condition leads to a venous modulation of the optical signal that has the same or similar frequency as the arterial one. Such conditions are generally difficult to effectively process because of the overlapping effects.

As described in the Aoyagi patent, the strength of each AC waveform may be estimated by measuring its size through, for example, a peak-to-valley subtraction, by a root mean square (RMS) calculations, integrating the area under the waveform, or the like. These calculations are generally least averaged over one or more arterial pulses. It is desirable, however, to calculate instantaneous ratios (RdAC/IrAC) that can be mapped into corresponding instantaneous saturation values, based on the sampling rate of the photopleth. However, such calculations are problematic as the AC signal nears a zero-crossing where the signal to noise ratio (SNR) drops significantly. For example, dividing two signals with low SNR values can render the calculated ratio unreliable, or worse, can render the calculated ratio undefined, such as when a near zero-crossing area causes division by or near zero. To try to avoid division by zero, the Ohmeda Biox pulse oximeter calculated the small changes between consecutive sampling points of each photopleth in order to get instantaneous saturation values. FIG. 3 illustrates various techniques used to try to avoid the foregoing drawbacks related to zero or near zero-crossing, including the differential technique attempted by the Ohmeda Biox.

Note that Ohmeda's differential technique is equivalent to a calculation over a derivative of the photopleth, and the derivative has the same low SNR problem whenever a flattened section of the photopleth is used in the ratios calculations. For example, the derivative will have a zero or near zero value and the RdAC/IrAC ratio will become unreliable or undefined, even in a substantially noise free signal. For example, FIG. 4 illustrates the derivative of the IrAC photopleth plotted along with the photopleth itself. As shown in FIG. 4, the derivative is even more prone to zero-crossing than the original photopleth as it crosses the zero line more often. Also, as mentioned, the derivative of a signal is often very sensitive to electronic noise. For example, according to "*Pulse Oximetry: Analysis of Theory, Technology, and Practice*," Journal of Clinical Monitoring, Vol. 4, October 1988, a published paper by the designers of the Ohmeda Biox, the calculated instantaneous saturations over some sections of the photopleth can be off by more than 50 percent (0/0) from the real value over a time as short as 1/10th of a second. As the designers described in their paper, this result is clearly an artifact of the signal processing technique employed in the Biox pulse oximeter since the blood saturation value can not change by that amount in 1/10th of a second.

Because of some of the foregoing drawbacks associated with the determination of instantaneous or point-by-point saturation from RdAC/IrAC ratios, designers now typically unequally weigh the calculated instantaneous saturation values over each photopleth, even when the photopleth is substantially noise free, with the consequence that a significant number of saturation values receive insignificant weights. This is tantamount to filtering out or ignoring valid signal data during the troublesome sections described above.

SUMMARY OF THE INVENTION

The result of the foregoing drawbacks is that the previous attempts fail to determine a stream of point-by-point saturation values. However, it is noteworthy that the sensitivity of the ratio calculation near a zero-crossing section of the waveform is not intrinsic to the photopleth itself, but rather an artifact of passing the detected signal through a high-pass filter. Accordingly, an aspect of the present invention includes a method of determining continuous and reliable calculations of the (RdAC/IrAC) ratio for each sampling point without concern for zero-crossing areas. As discussed in the foregoing and disclosed in the following, such determination of continuous ratios is very advantageous, especially in cases of venous pulsation, intermittent motion artifacts, and the like. Moreover, such determination is advantageous for its sheer diagnostic value.

For purposes of summarizing the invention, certain aspects, advantages and novel features of the invention have been described herein. Of course, it is to be understood that not necessarily all such aspects, advantages or features will be embodied in any particular embodiment of the invention.

BRIEF DESCRIPTION OF THE DRAWINGS

A general architecture that implements the various features of the invention will now be described with reference to the drawings. The drawings and the associated descriptions are provided to illustrate embodiments of the invention and not to limit the scope of the invention.

FIG. 32 illustrates magnitudes of complex frequency ratios calculated from the fundamental and harmonics of the photopleths of FIG. 2.

FIG. 33 illustrates frequency transformed photopleths and phases of the corresponding ratios.

DETAILED DESCRIPTION OF THE PREFERRED EMBODIMENT

Figure 1:
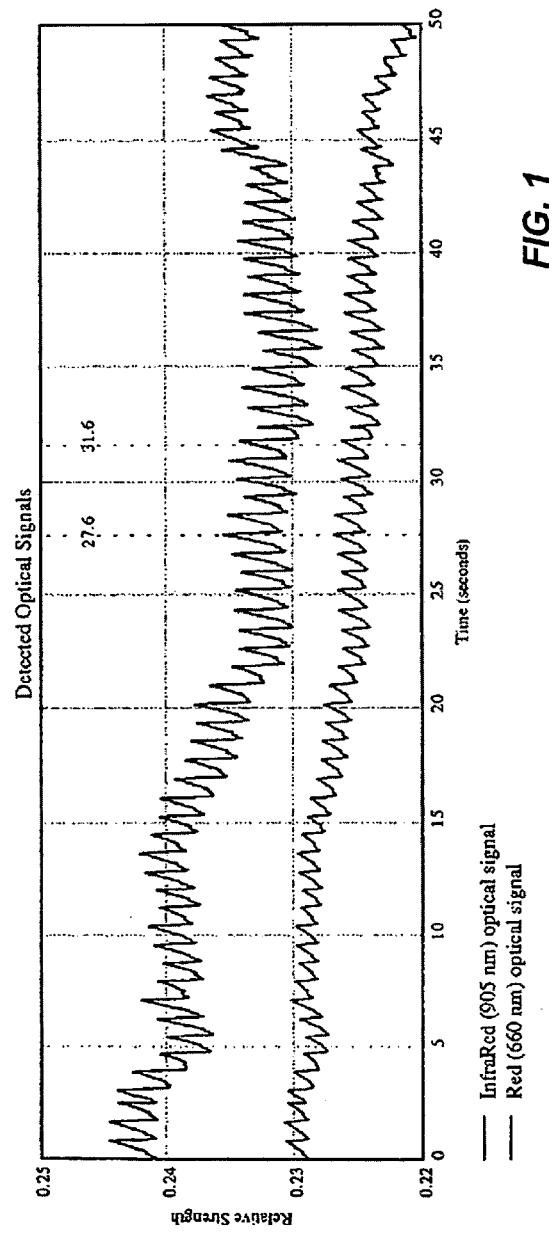
FIG. 1 illustrates a photopleths including detected Red and Infrared signals.

Complex numbers were generally invented/discovered in the 1500's by Galiermo Cardano in Italy as he was struggling to solve a general third order polynomial equation. Later, Argand suggested that each complex number may be represented as a point in a plane where its imaginary part is plotted on the Y-axis and its real part on the X-axis, this is referred to as the Cartesian form of a complex number. An alternate representation of complex numbers is called the polar form where a magnitude and an angle can designate a unique point in the Argand plane, hence representing a complex number. Although mathematicians at that time looked at complex numbers with great suspicion, it turned out that they were useful for the general solutions of polynomial equations and applicable in such diverse fields as quantum mechanics to describe the state of elementary particles.

In the field of electrical engineering, students learn that circuit analysis, under alternating voltage conditions, can be significantly simplified if the concept of complex currents and voltages is introduced. When a voltage is applied to an electrical element, a current is caused to pass through it. Dividing the applied voltage by the corresponding current gives the resistance of the electrical element. In the complex domain, dividing the complex voltage by the complex current give rise to a complex form of resistance called "impedance," which is represented again by a complex number. The real part of the impedance is the resistance while the complex part is related to capacitance and inductance. The complex part affects the phase, lead or lag, of the driving signals. It can be shown that the response of a linear system to a sinusoidal excitation is a sinusoid with the same frequency but generally of different amplitude and phase. A resistor element, for example, affects the amplitude only, whereas a capacitor or an inductor affects the phase. A combination of resistors, capacitors and/or inductors can affect the amplitude as well as the phase of the driving excitation and are considered examples of a linear system. Since each complex number consists of amplitude and phase, it is natural that they be used to encode the amplitude and phase and track their evolution throughout a linear system. Therefore, when a linear system is driven by a complex excitation, its output will be the same complex input multiplied by a complex scaling factor that scales its amplitude appropriately and adds a certain phase in accordance with the rules of complex multiplication. Note that the phase in this context is a relative one between two fundamental variables of the system, e.g. for an electrical circuit they might be voltage and current at a certain node of the circuit, or output voltage and input voltage, or the like.

In pulse oximetry, there is no direct analog for voltages or currents. Generally, pulse oximetry deals with two highly correlated optical signals, e.g., the Red and Infrared signals, with fundamentally little or no discernible phase difference. Thus, encoding those signals as complex numbers seems to add little or no value to the signal processing. However, there are several conditions under which a variable phase difference may be introduced between the Red and Infrared signals. For example, motion artifacts create a condition where the sensor may decouple from the skin. In such a condition, the detected optical signals will have components that depend on the refraction through the sensor material itself instead of the wavelength of light, as well as the desired components that have traveled through the vascular bed. Venous pulsation creates another condition, which, as disclosed in the foregoing, affects the phase difference. Under the foregoing conditions where the phase is changing, use of complex number encoding provides advantages in signal processing, including providing the ability to continuously monitor the arterial saturation vs. time without concern about signal zero-crossing, as disclosed in the following.

A Hilbert Transformer is a signal processing technique that takes a real signal and converts it into a related signal which has its frequency components shifted by $\pi/2$ radians for positive frequencies, and by $-\pi/2$ radians for negative frequencies, without affecting their respective amplitudes. The book, "*Theory and Application of Digital Signal Processing*, Prentice-Hall, Inc.," by Rabiner and Gold, introduces the subject. Formation of a complex signal is accomplished by considering the original signal itself as the real part of a complex signal and the output of the Hilbert Transformer as the imaginary part of the same complex signal. Such signals are generally referred to as an "analytical signal" in the signal processing field because the magnitudes of its negative frequencies are equal to zero. In the context of pulse photometry, we shall refer to such a complex signal as complex photopleth or complex AC.

It is noteworthy that the prior methodology of seeking a derivative of a signal shifts that signal's components by $\pi/2$ radians, similar to the Hilbert transform. However, the derivative of a signal also multiplies each corresponding amplitude by the value of the radian frequency $\omega$, thus magnifying the signal's frequency components as the components increase in frequency. Thus, the derivative is often more sensitive to electronic noise. In contrast, the Hilbert Transformer generally has a flat response with respect to frequency. However, a skilled artisan will recognize other transforms, derivatives, or the like, can be used to encode the imaginary part of the complex photopleth.

Figure 2:
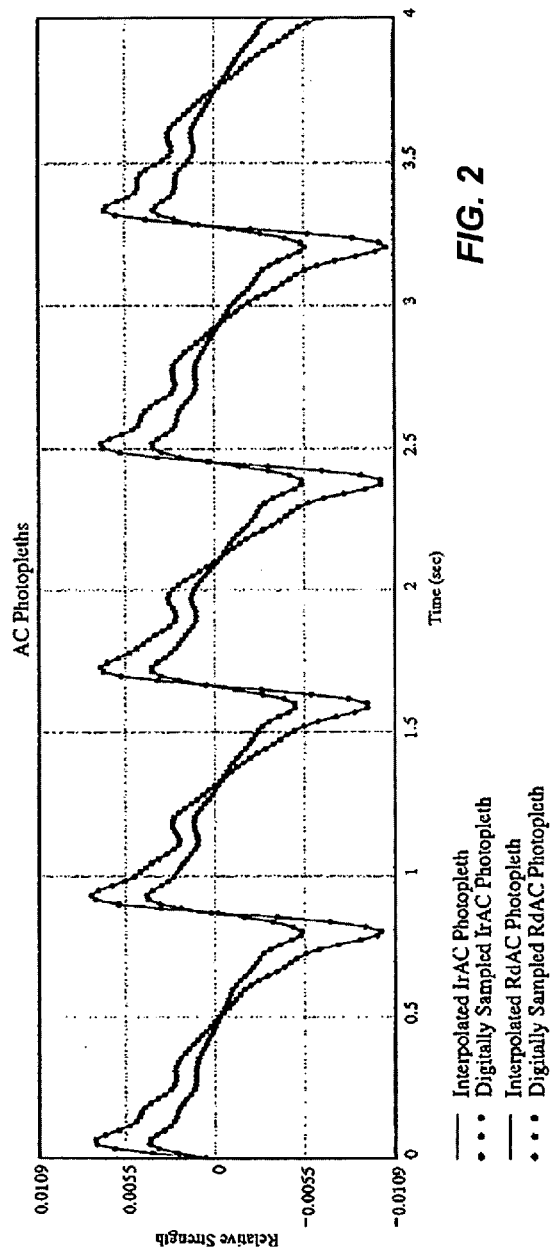
FIG. 2 illustrates the photopleths of FIG. 1, after it has been normalized and bandpassed.
Figure 5:
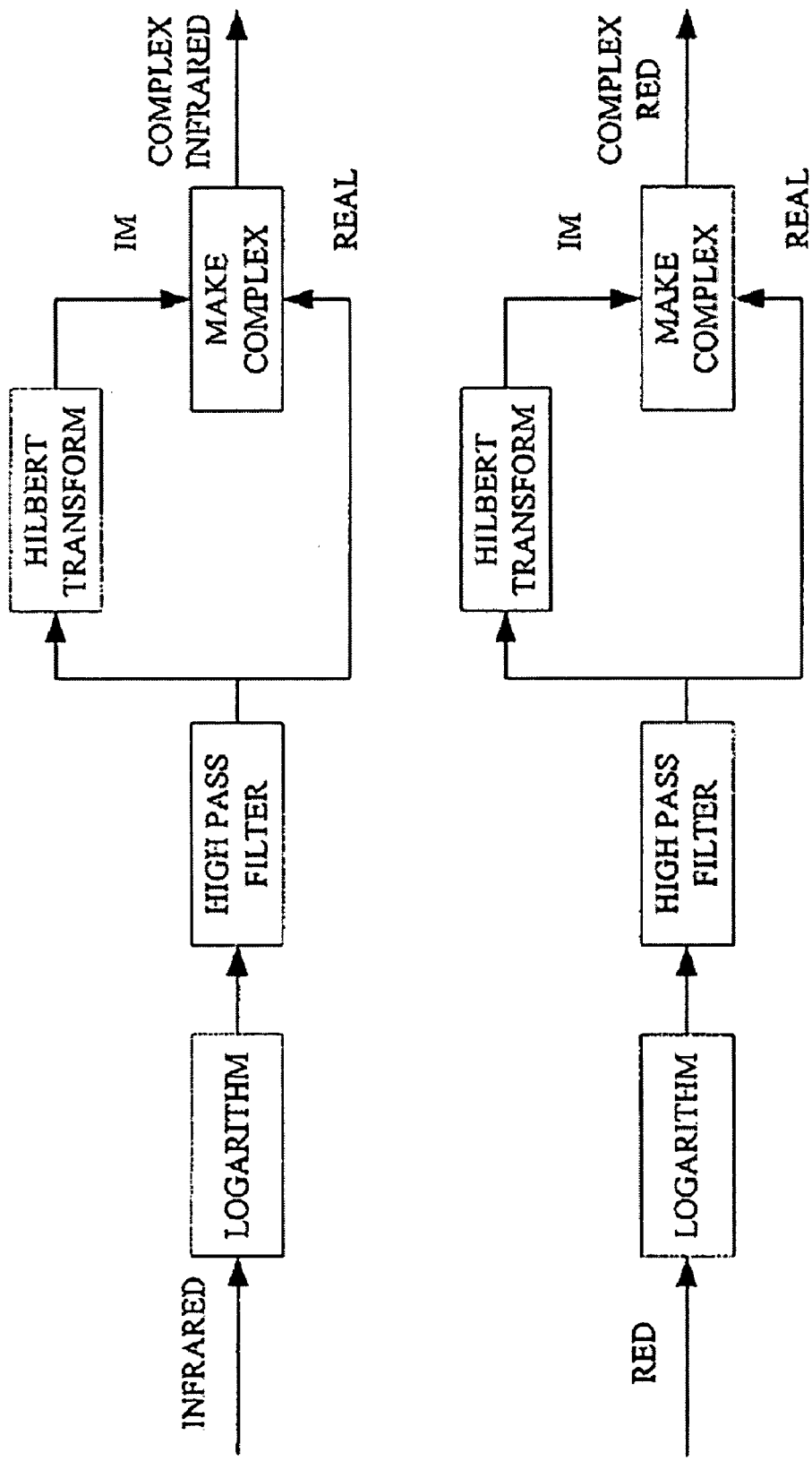
FIG. 5 illustrates a block diagram of a complex photopleth generator, according to an embodiment of the invention.
Figure 5A:
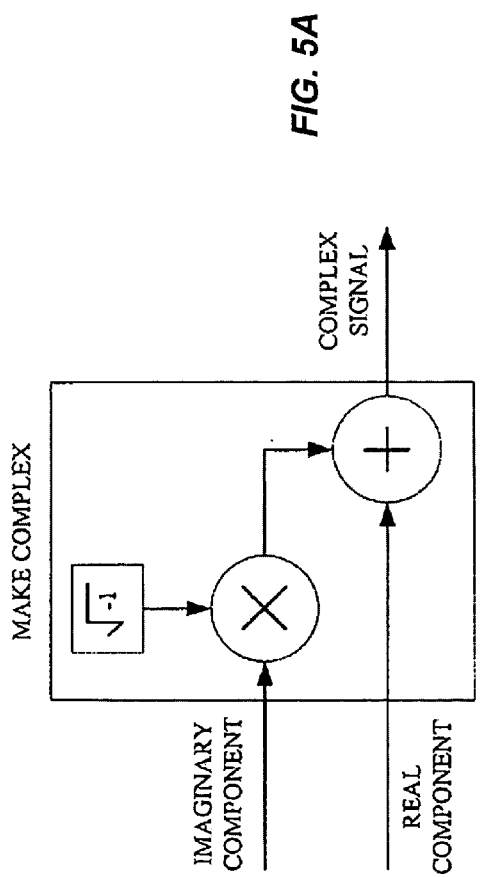
FIG. 5A illustrates a block diagram of a complex maker of the generator of FIG. 5.
Figure 7:
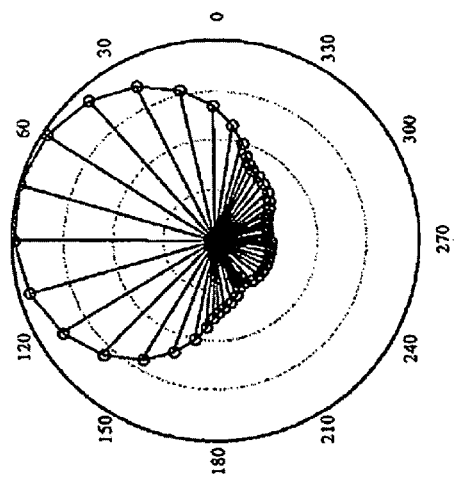
FIG. 7 illustrates an area calculation of the complex photopleths of FIG. 5.
Figure 6:
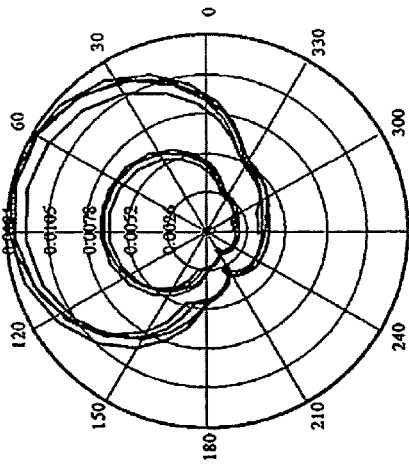
FIG. 6 illustrates a polar plot of the complex photopleths of FIG. 5.

When the foregoing complex encoding is applied to both RdAC and IrAC photopleths, as shown in a complex photopleth generator of FIG. 5, then both complex RdAC and IrAC are in phase. As shown in FIG. 5, the complex photopleth generator 500 includes one or more log filters 502, one or more high pass filters 504, one or more Hilbert transformers 506, and one or more complex makers 508. The log and high pass filter 502 and 508 generally normalize and filter the signals, as disclosed in the foregoing with reference to FIG. 2. The Hilbert transformers 506 converts the real signal into related signals shifted by $\pi/2$ and $-\pi/2$ radians, also as disclosed in the foregoing. The complex makers 508 combine the output of the Hilbert transformers 506 with the input of the Hilbert transformers 506 to generate complex in phase photopleths, generally referred to herein as type "A" complex signals, as shown in FIG. 5A. FIGS. 6 and 7 illustrate polar plots of the complex photopleths generated from the generator 500 of FIG. 5.

Figure 8:
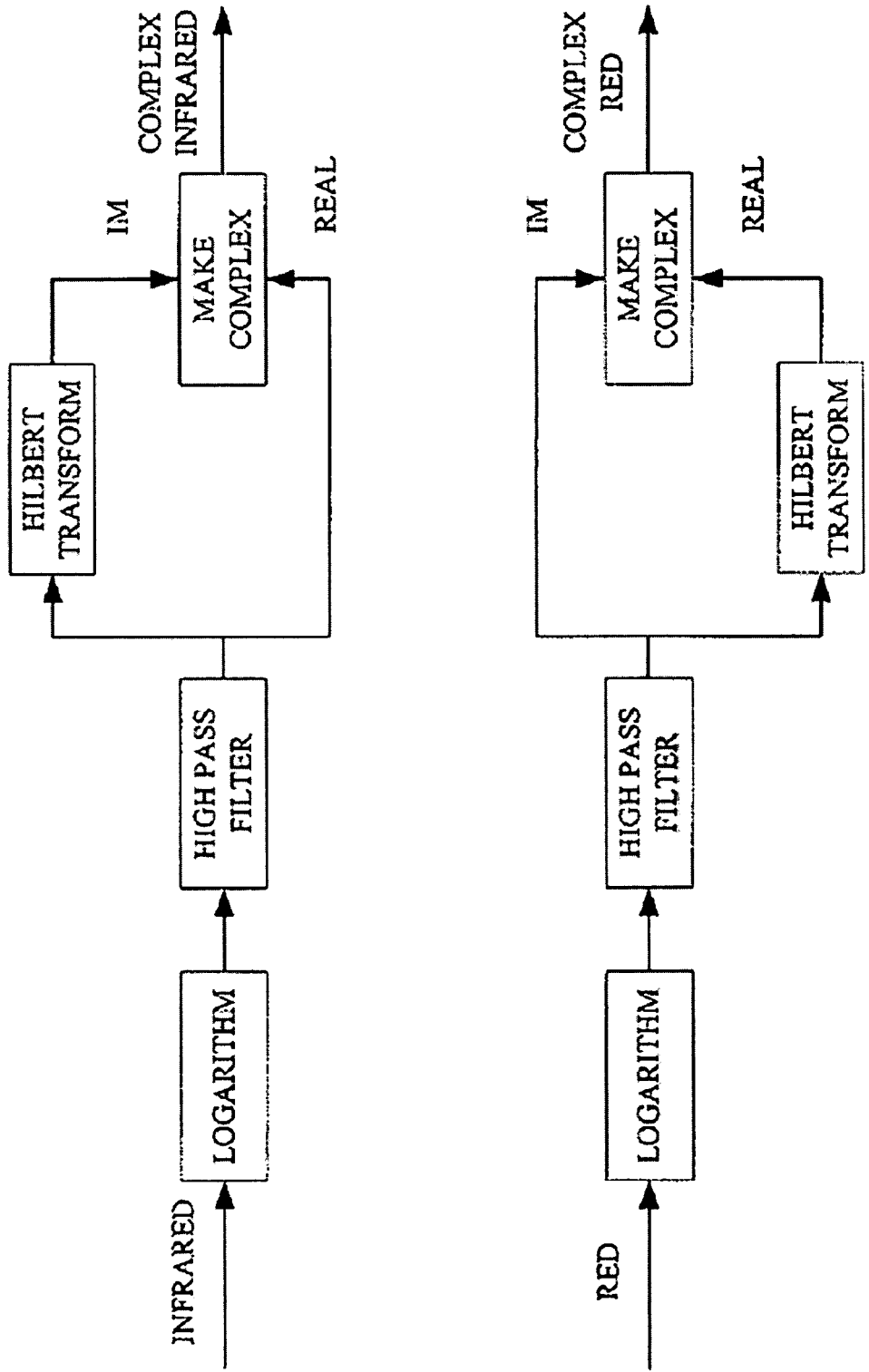
FIG. 8 illustrates a block diagram of another complex photopleth generator, according to another embodiment of the invention.
Figure 10:
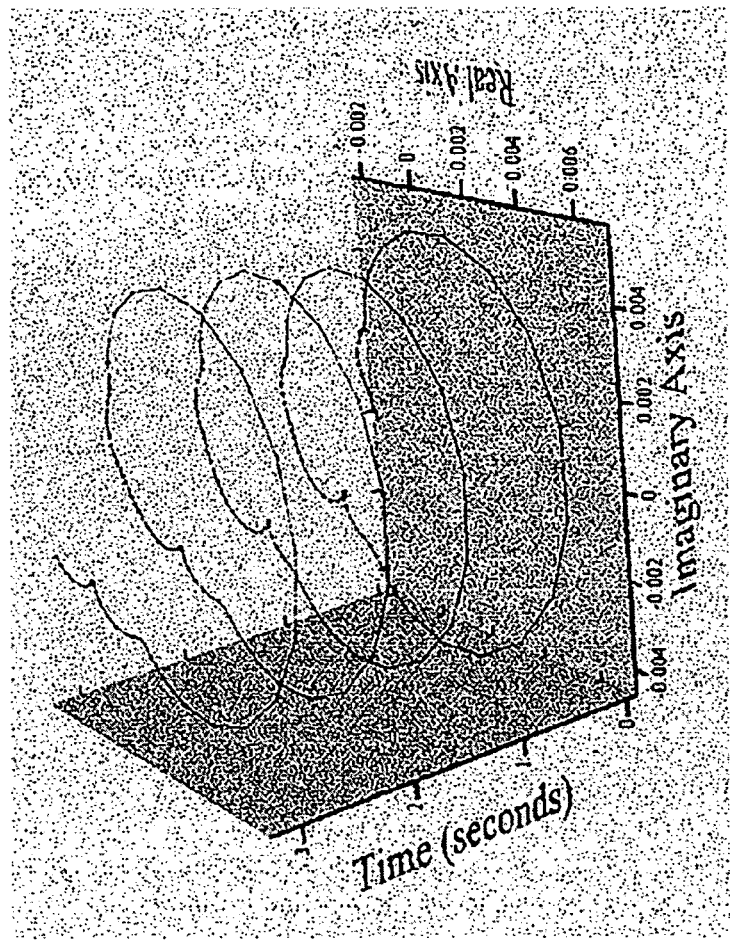
FIG. 10 illustrates a three-dimensional polar plot of the complex photopleth of FIG. 8.
Figure 9:
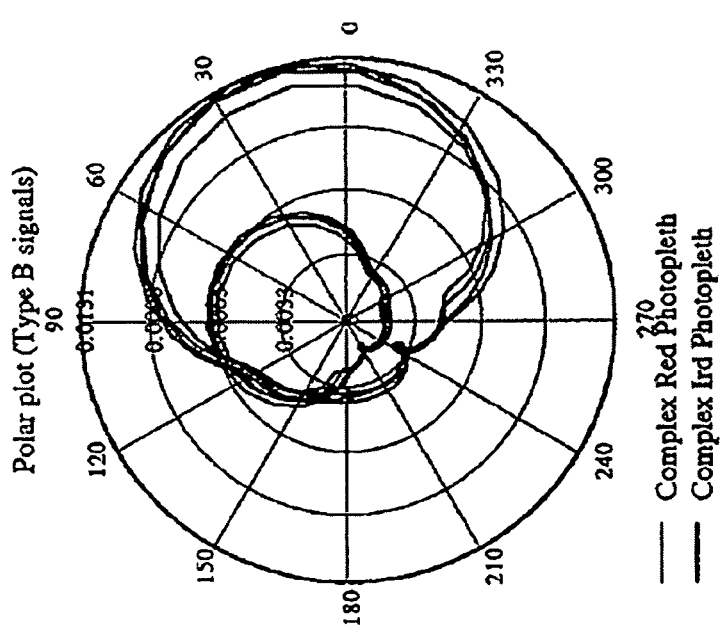
FIG. 9 illustrates a polar plot of the complex photopleth of FIG. 8.

FIG. 8 illustrates a complex photopleth generator 800, according to another embodiment of the invention. As shown in FIG. 8, the generator 800 includes the one or more log filters 502, the one or more high pass filters 504, the one or more Hilbert transformers 506, and the one or more complex makers 508 disclosed with respect to FIG. 5. However, in the generator 800, the Hilbert transformer 506 accepting the exemplary Red signal encodes the real components of the RdAC signal rather than the complex components. Thus, the generator 800 of FIG. 8 generates a complex photopleth, generally referred to herein as type "B" complex signals. FIGS. 9 and 10 illustrate polar plots of the complex photopleths generated from the generator 800 of FIG. 8. Note that as time progresses, the locus of the complex points rotates around the origin but does not pass through it, regardless of type A or type B complex signals. Accordingly, the strength of each of the foregoing AC photopleth complex signals can be encoded in their respective magnitudes, which is the length between the origin and any point on the complex waveform in FIGS. 6, 7, 9 and 10. The morphology of the complex signals depend on the condition of the subject, such as, for example, age, blood pressure, arterial impedance, posture, or the like.

Based on the foregoing disclosure, the complex photopleths of FIGS. 6, 7, 9 and 10 can be classified with techniques like the "Slant Line Transform" or other classification techniques available in the field of image recognition or the like. Such classification techniques can be advantageously employed to help reject photopleths that are corrupted by noise, which can be an invaluable during episodes of motion artifacts.

Generating Complex Ratios

Figure 11:
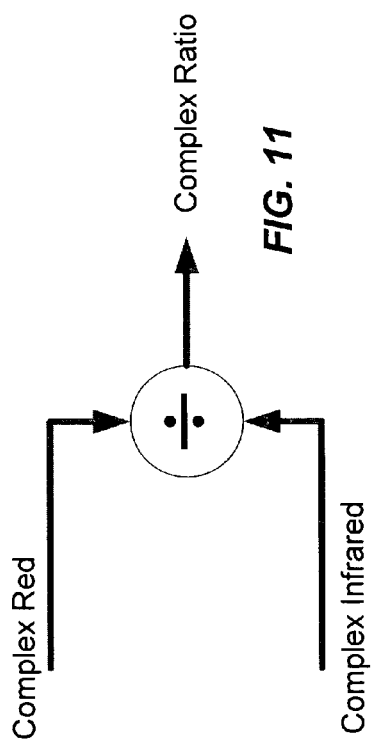
FIG. 11 illustrates a block diagram of a complex ratio generator, according to another embodiment of the invention.

FIG. 11 illustrates a complex ratio generator 1100 for generating what will generally be referred to as the "complex ratio." The complex ratio is a point-wise complex division of type A or type B RdAC and IrAC complex photopleth signals. The magnitude of each division carries along with it the conventional (RdAC/IrAC) ratio, in addition, its phase encodes the angle variation between the Red and Infrared signals, which as disclosed in the foregoing, can generally be equal to zero for undisturbed signals. Different plots in the complex plane result depending upon whether type A or type B complex waveforms are used to generate the complex ratios. The different plots also enable or suggest different types of signal processing, examples of which are disclosed as follows.

Figure 12:
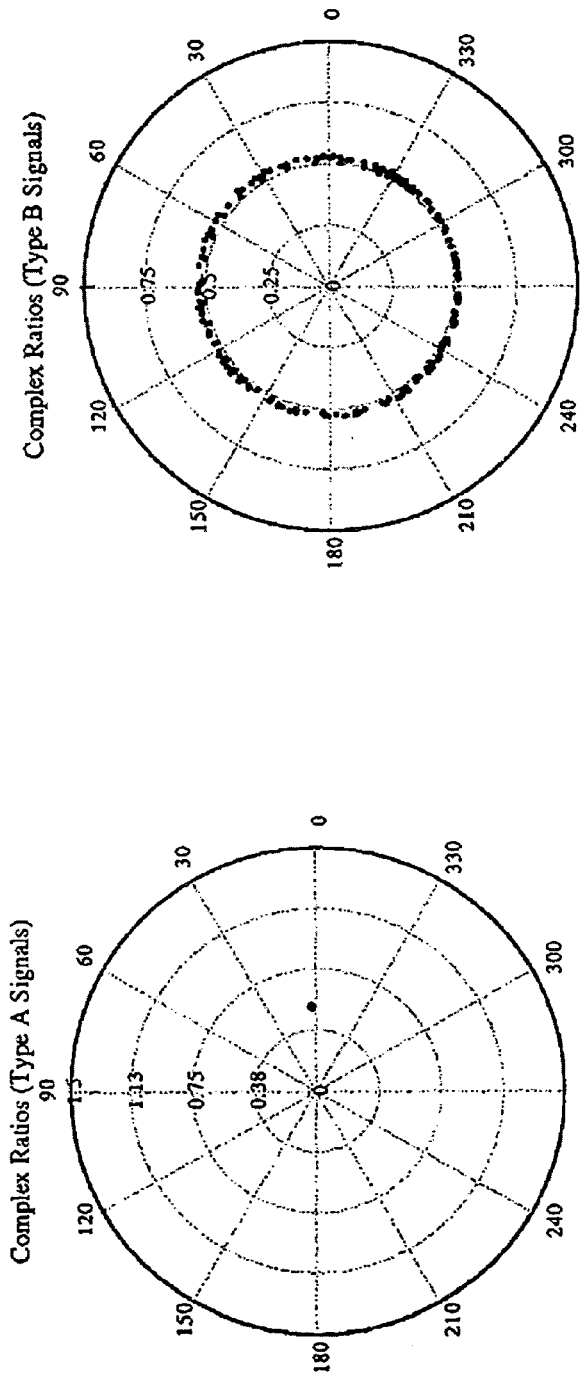
FIG. 12 illustrates complex ratios for the type A complex signals illustrated in FIG. 6.
Figure 19:
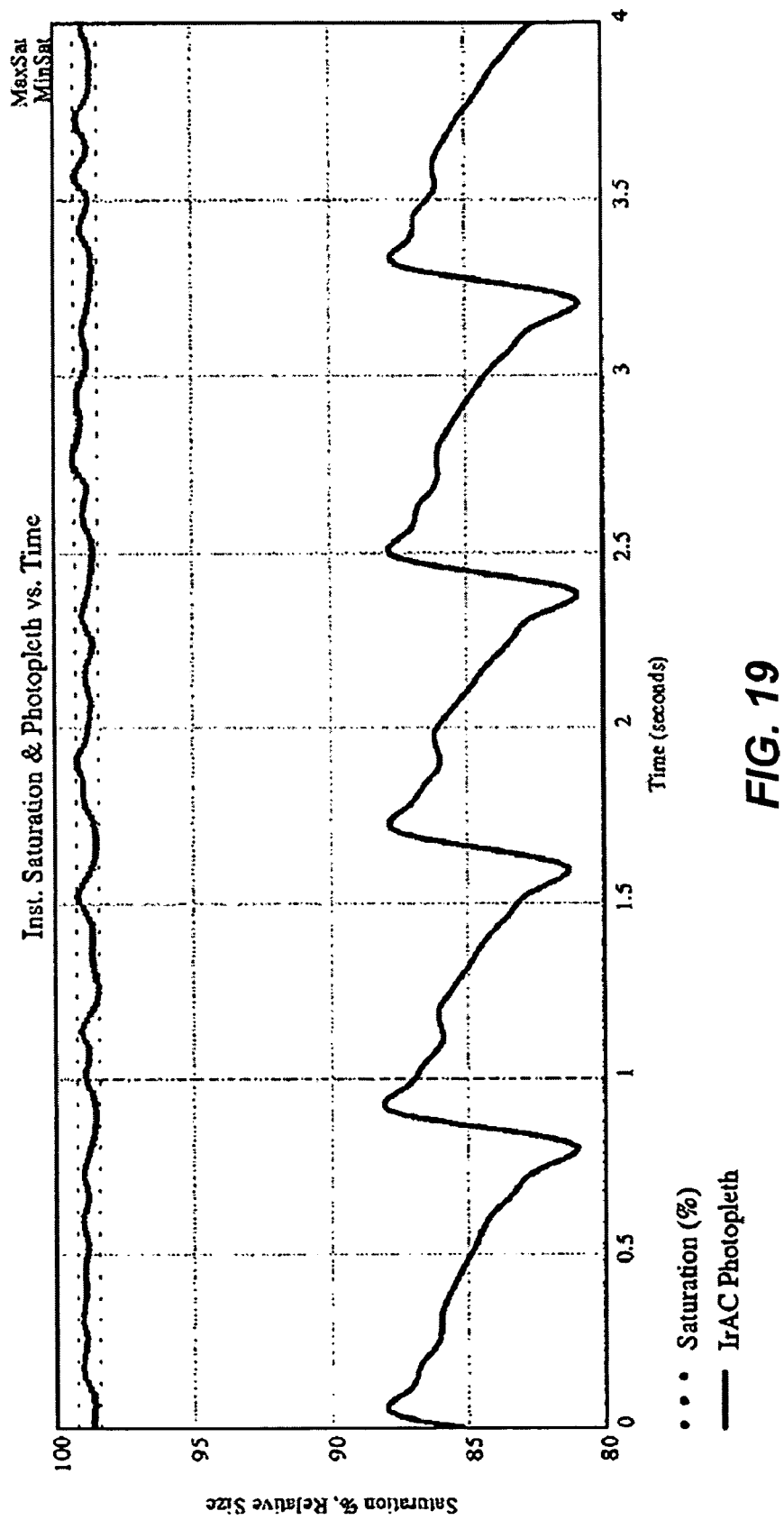
FIG. 19 illustrates a plot of the instantaneous saturation of the data used to generate the complex ratios shown in FIG. 12, as well as the corresponding complex photopleth from which the saturation was calculated.
Figure 20:
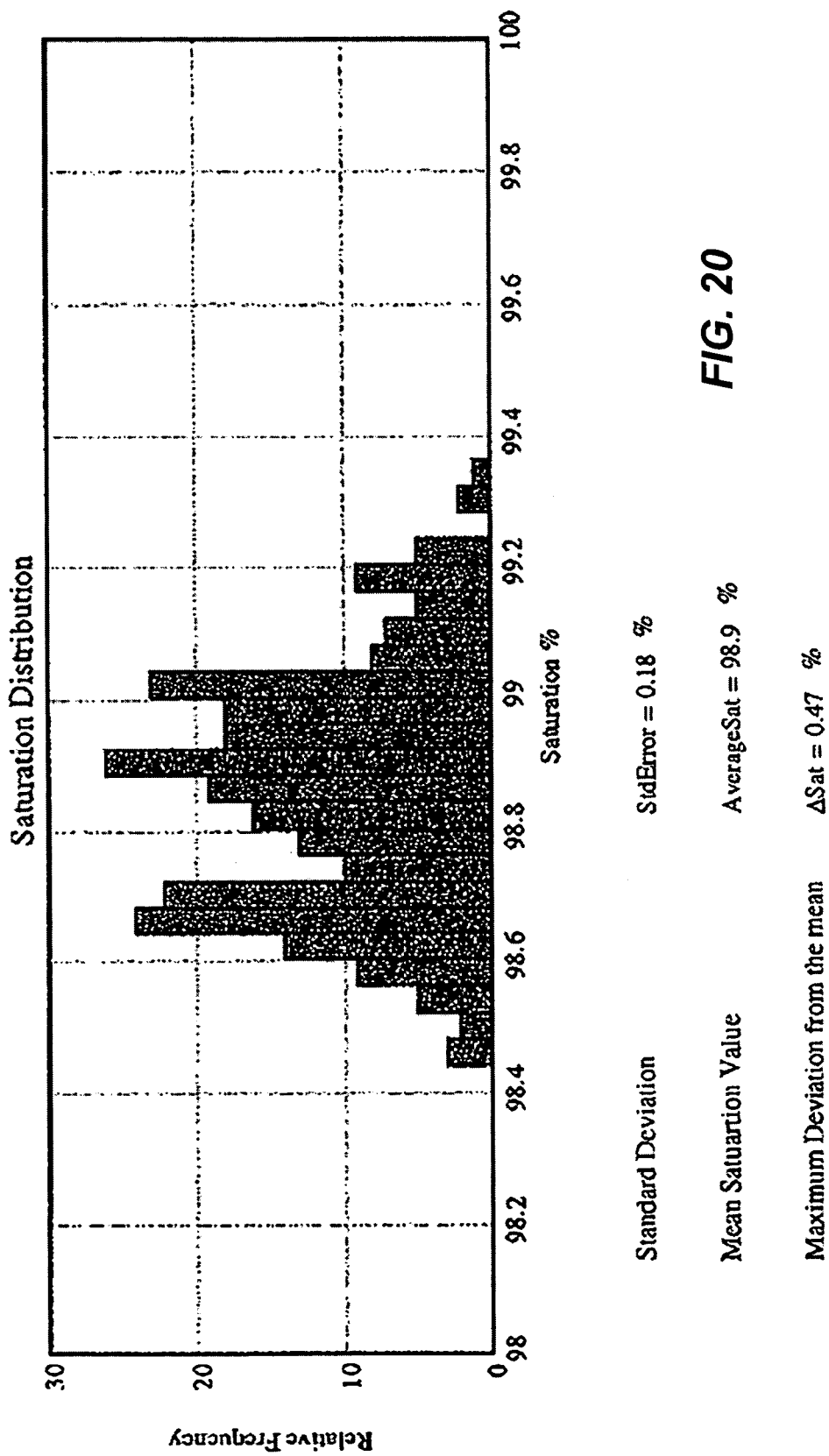
FIG. 20 illustrates an expanded view of the saturation distribution results of FIG. 19.

For example, when the arterial saturation is constant and type A complex waveforms are generated, the complex ratio plot in the complex plane looks like a fuzzy point very close to the real axis, as shown in FIG. 12. This is remarkable for it indicates, unlike previous techniques, that the instantaneous ratios over one or several photopleths are nearly constant throughout, which matches the input signal data, i.e., that the saturation is constant. FIG. 19 illustrates a plot of the instantaneous saturation vs. time of the data used to generate the complex ratios shown in FIG. 12, as well as the corresponding photopleth from which the saturation was calculated. Note that the saturation is generally calculated from the magnitudes of the complex ratios vs. time. Also, FIG. 20 illustrates that the maximum deviation from the mean value of the saturation is less than about 0.5 percent (%), which compares favorably to the more than about 50 percent (%) variations calculated using the Biox algorithm. Moreover, FIG. 20 illustrates that the standard deviation of the saturation is a mere about 0.18 percent (%). These results clearly and advantageously indicate that weighing or filtering is not needed to utilize the data, and that all points in the photopleth can be useful in the subsequent analysis.

Figure 13:
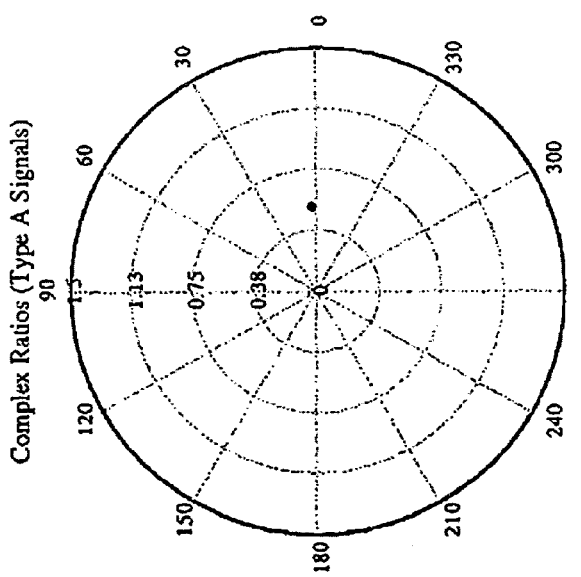
FIG. 13 illustrates complex ratios for the type B complex signals illustrated in FIG. 9.
Figure 14:
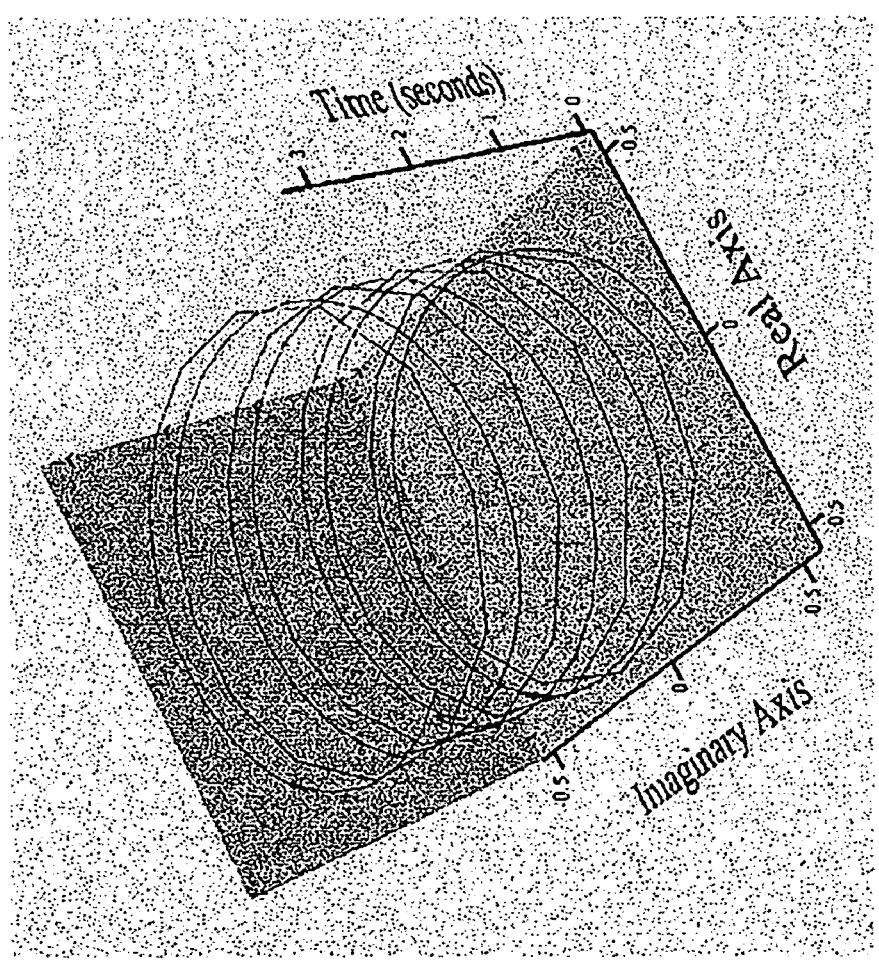
FIG. 14 illustrates the complex ratios of FIG. 13 in three (3) dimensions.

FIG. 13 is a plot of the complex ratios generated by the photopleths used to generate FIG. 12, but with type B complex waveforms. As shown in FIG. 13, the constant saturation translated into a circle of fixed radius in the complex plane. A myriad of mapping techniques available in the field of complex analysis can be brought to bear to help analyze this type of signal. For example, the logarithm function may be used to map a circle in the complex plane into a line in the same complex plane. FIG. 14 depicts a 3D plot of complex ratios vs. time, where time is plotted along the vertical 'Z' axis. As shown in FIG. 14, a constant ratio, i.e. constant saturation, is reflected as a uniform helix.

Generating Confidence Measures

Figure 15:
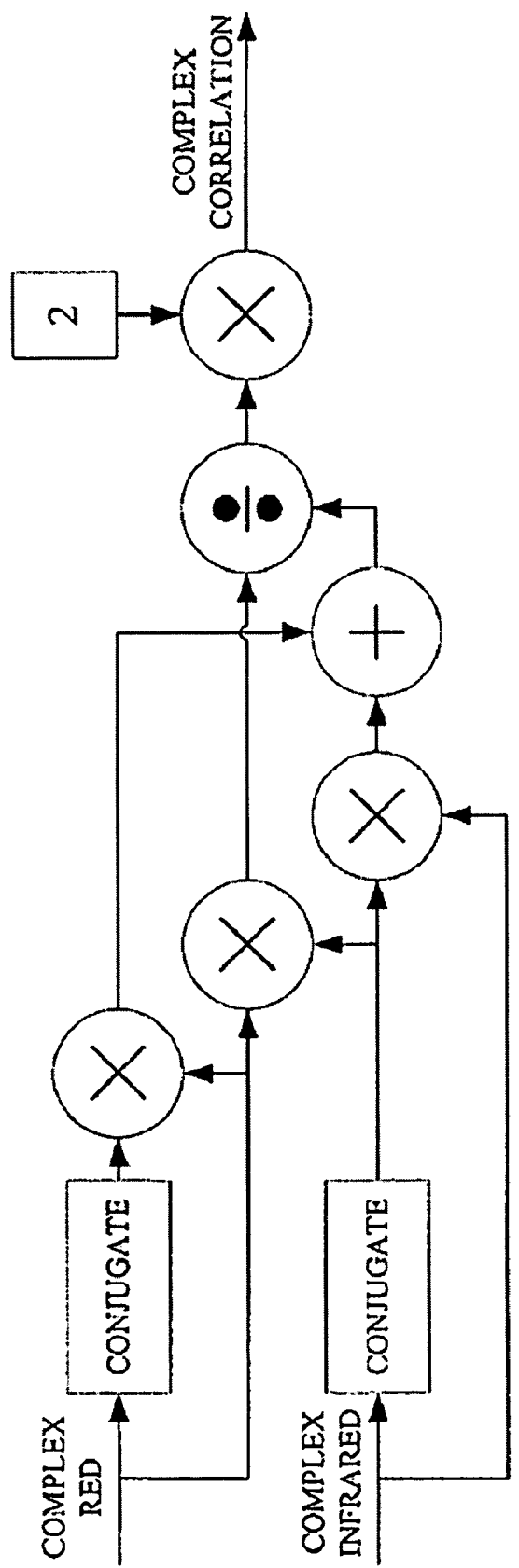
FIG. 15 illustrates a block diagram of a complex correlation generator, according to another embodiment of the invention.

Normally, each of the instantaneous complex ratio values are valid and reliable. However, certain physiological or patient motion conditions may render a some or all of the calculated ratios unusable. Therefore, it is desirable to provide confidence measures by which such unreliable points may be discarded, filtered or corrected. Toward that end, FIG. 15 illustrates a complex correlation generator 1500, which includes one or more conjugate generators 1502, one or more signal multipliers 1504, signal adders 1506 and signal dividers 1508. As shown in FIG. 15, the complex RdAC and the complex IrAC are input into the generator 1502. The complex RdAC is multiplied by the conjugate of the complex IrAC. This product is divided by the sum of the complex IrAC multiplied with its conjugate, and the product of the complex RdAC and its conjugate. The resulting signal is then multiplied by the scalar two (2) to form a measure of the complex correlation, such as, for example, a complex confidence number associated with each calculated complex ratio.

Figure 17:
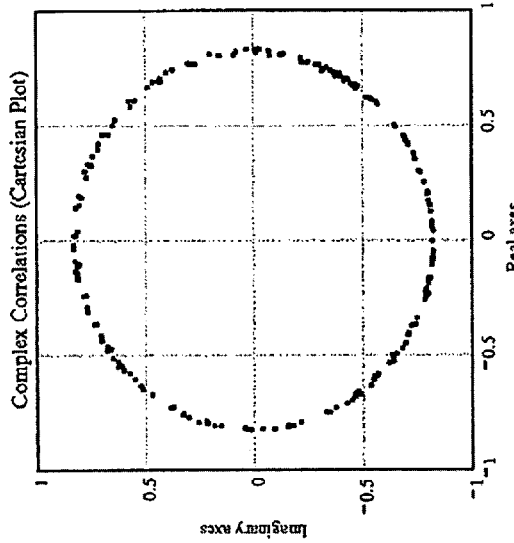
FIG. 17 illustrates complex correlations generated by the complex correlation generator of FIG. 15.
Figure 16:
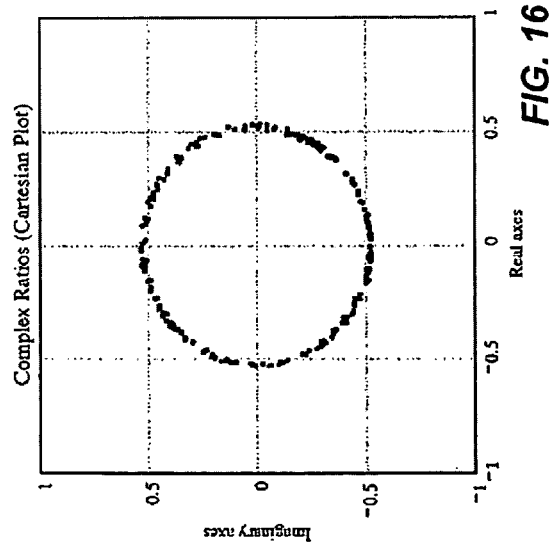
FIG. 16 illustrates complex ratios generated by the complex ratio generator of FIG. 11 using the complex signals generated by the generator of FIG. 8.
Figure 18:
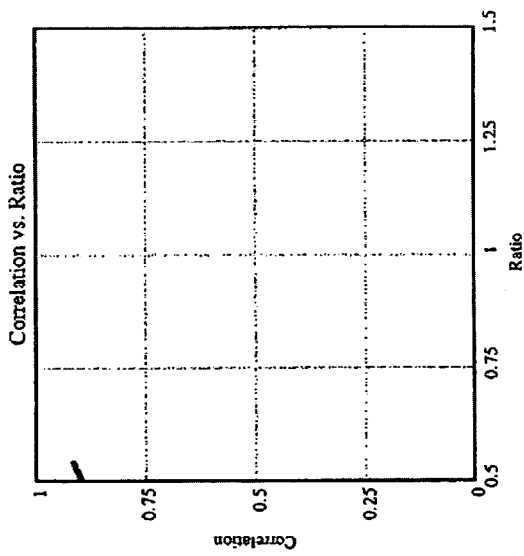
FIG. 18 illustrates the square root of the magnitude of the complex ratios of FIG. 16 vs. the complex correlations of FIG. 17.

This confidence may be used to gate or preferentially weigh each corresponding complex ratio in a filtering technique to provide more reliable saturation values. For example, FIG. 16 depicts a plot of instantaneous complex ratios calculated over several seconds and FIG. 17 depicts the instantaneous complex correlations associated with the calculated complex ratios. FIG. 18 depicts the joint relationship between the calculated complex ratios of FIG. 16 and associated the complex correlation of FIG. 17. Note that a certain correlation threshold may be established below which all data point can be rejected, thereby advantageously enhancing the final saturation estimation. Note that in FIG. 18, all the data points are acceptable. Situations where not all data points are acceptable, e.g. abnormal waveforms or motion artifacts, will be disclosed in the following.

The phase of the instantaneous complex ratios may also be used to assign a confidence measure to each complex ratio value. Typically the phase value should be very close to zero in the case of complex ratios generated from type A complex waveforms, as shown in FIG. 12. However, example of the use of the phase in the filtering of unreliable complex ratios under the effects of motion artifacts will also be discussed in the following.

Implementing Filtering Techniques

Figure 3:
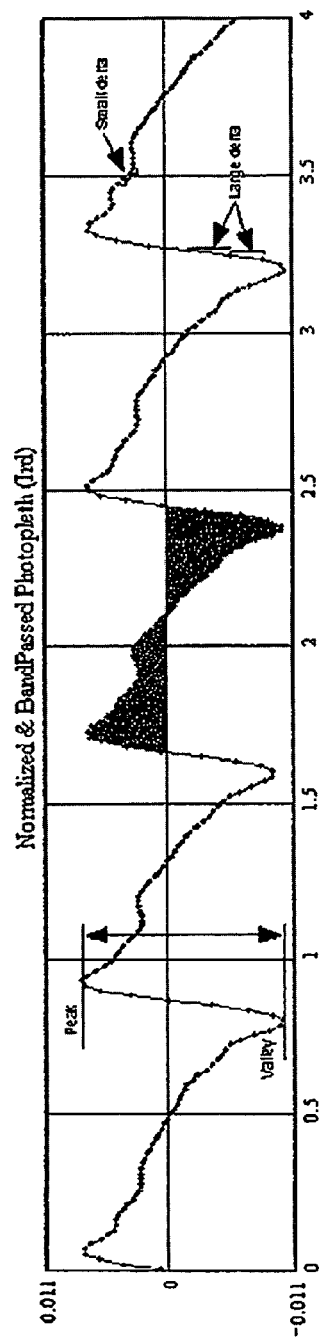
FIG. 3 illustrates conventional techniques for calculating strength of one of the photopleths of FIG. 2.
Figure 4:
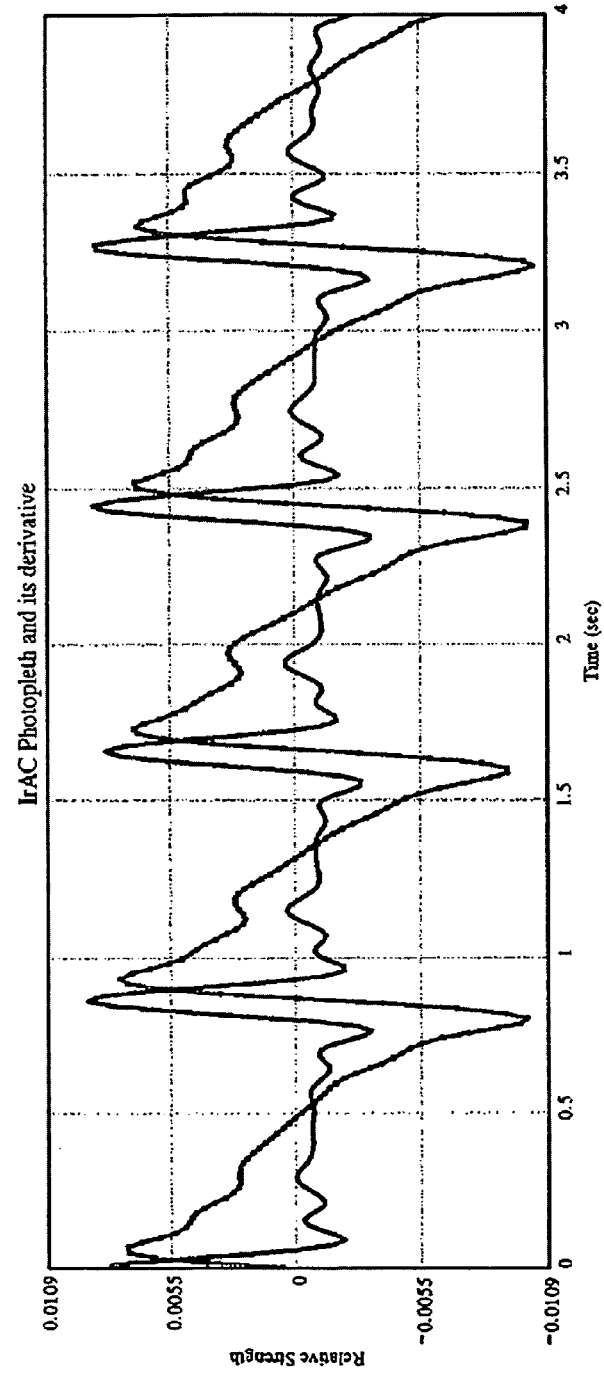
FIG. 4 illustrates the IrAC photopleth of FIG. 2 and its derivative.
Figure 4A:
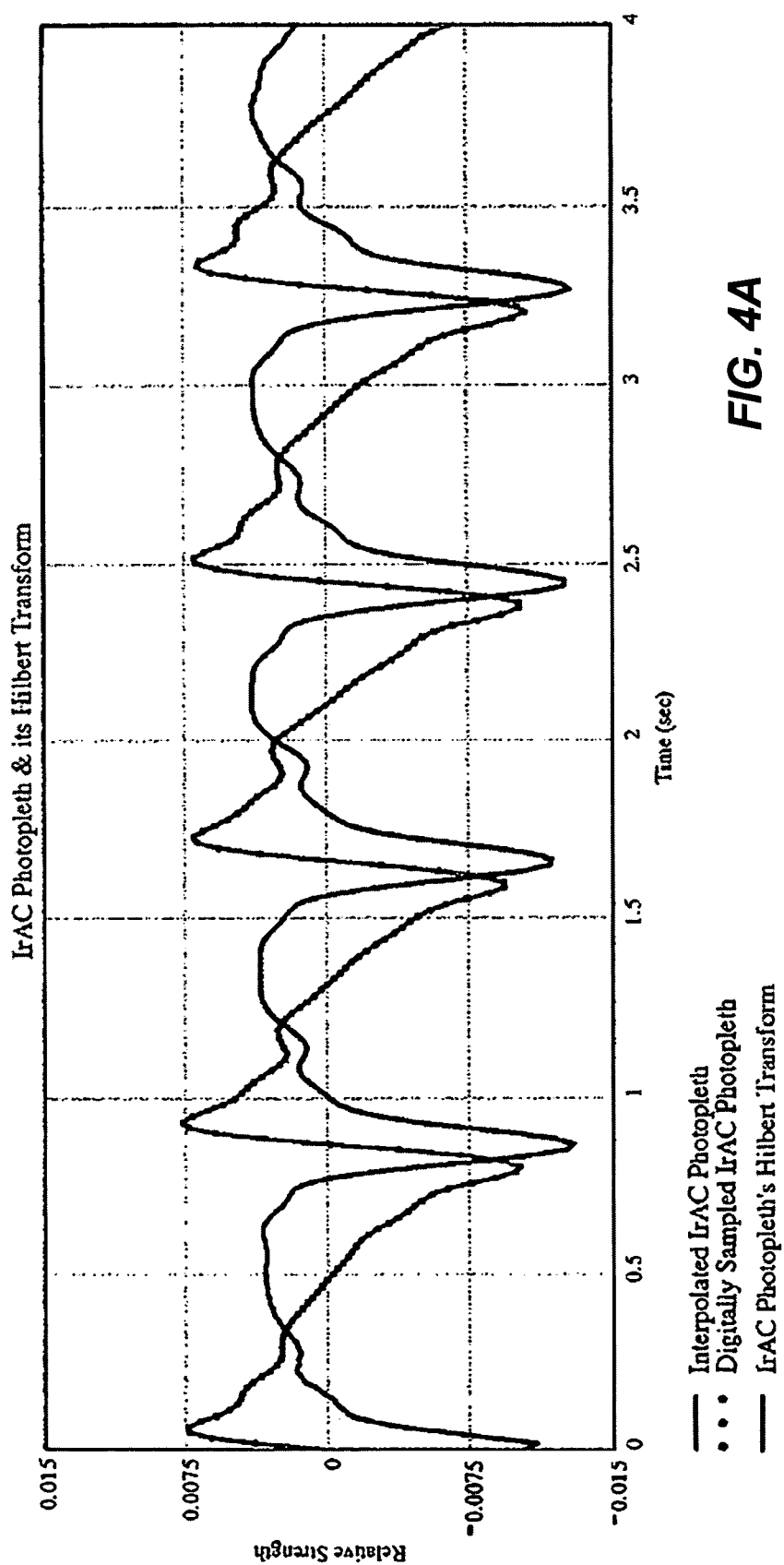
FIG. 4A illustrates the photopleth of FIG. 1 and its Hilbert transform, according to an embodiment of the invention.

Once the complex waveforms or their corresponding instantaneous complex ratios or saturation values are available, a myriad of linear, nonlinear and statistical filtering techniques may be applied to reliably estimate the blood saturation values. For example, when simple averaging is desired, the areas of the complex photopleth waveforms shown in FIG. 6 can be calculated over a certain span of time or integral number of pulses. The ratio between two values corresponding to the Red and Infrared waveforms' areas is calculated, the result of which can then be used to calculate the blood saturation value. Note that this is the analog of integrating the area of the Red and Infrared photopleths shown in FIG. 2 then taking their ratios. FIG. 3 shows an example of area integration of one real waveform. For the case of a complex waveform the area can be estimated by summing the individual areas of triangles that constitute the complex waveform, as shown in FIG. 7. Introductory calculus textbooks may be consulted on the subject of area integration. This technique does not require the use of complex ratios, rather straightforward real number division of waveform areas can be used.

Another powerful filtering technique takes advantage of the abundance of ratios values available over short period of time. For example, the continuous stream of instantaneous ratio or saturation values can be fed into a weighing filter along with their associated confidence values. The filter can then discard or appropriately weigh the corresponding value of the ratio or the saturation. The high number of values, e.g., 62.5 values per second in the present embodiment, available to the filter makes it more likely that some of them will be within an acceptable limit despite the affect of disturbances or noise.

Statistical techniques such as frequency distribution analysis can further be used alone or in combination with the previous techniques to estimate the true blood saturation values. Exemplary techniques where the statistics of the distribution of the ratio or saturation values can be used to extract a more accurate estimation of the true saturation value, as disclosed in the following.

Managing Abnormal Waveforms

Figure 21:
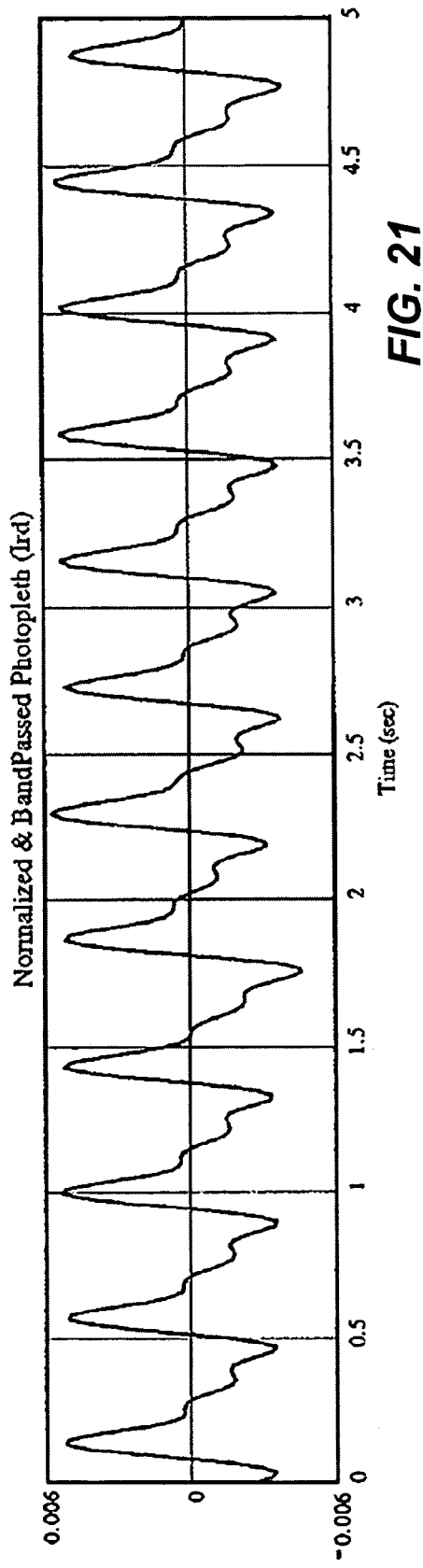
FIGS. 21 and 22 illustrate Infrared and Red photopleths, respectively, modulated by venous pulsation.
Figure 22:
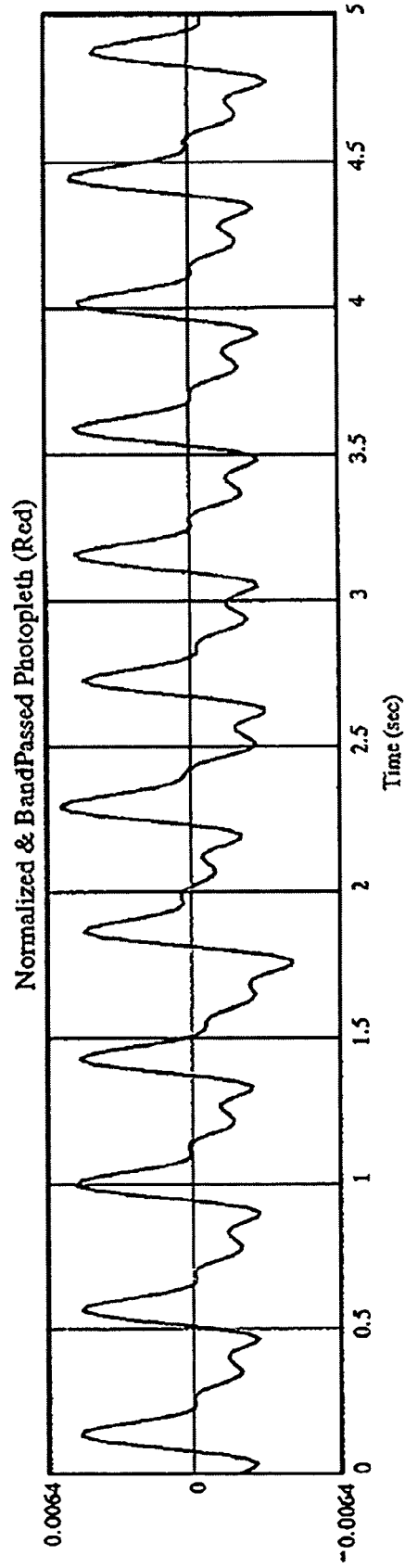
Figure 23:
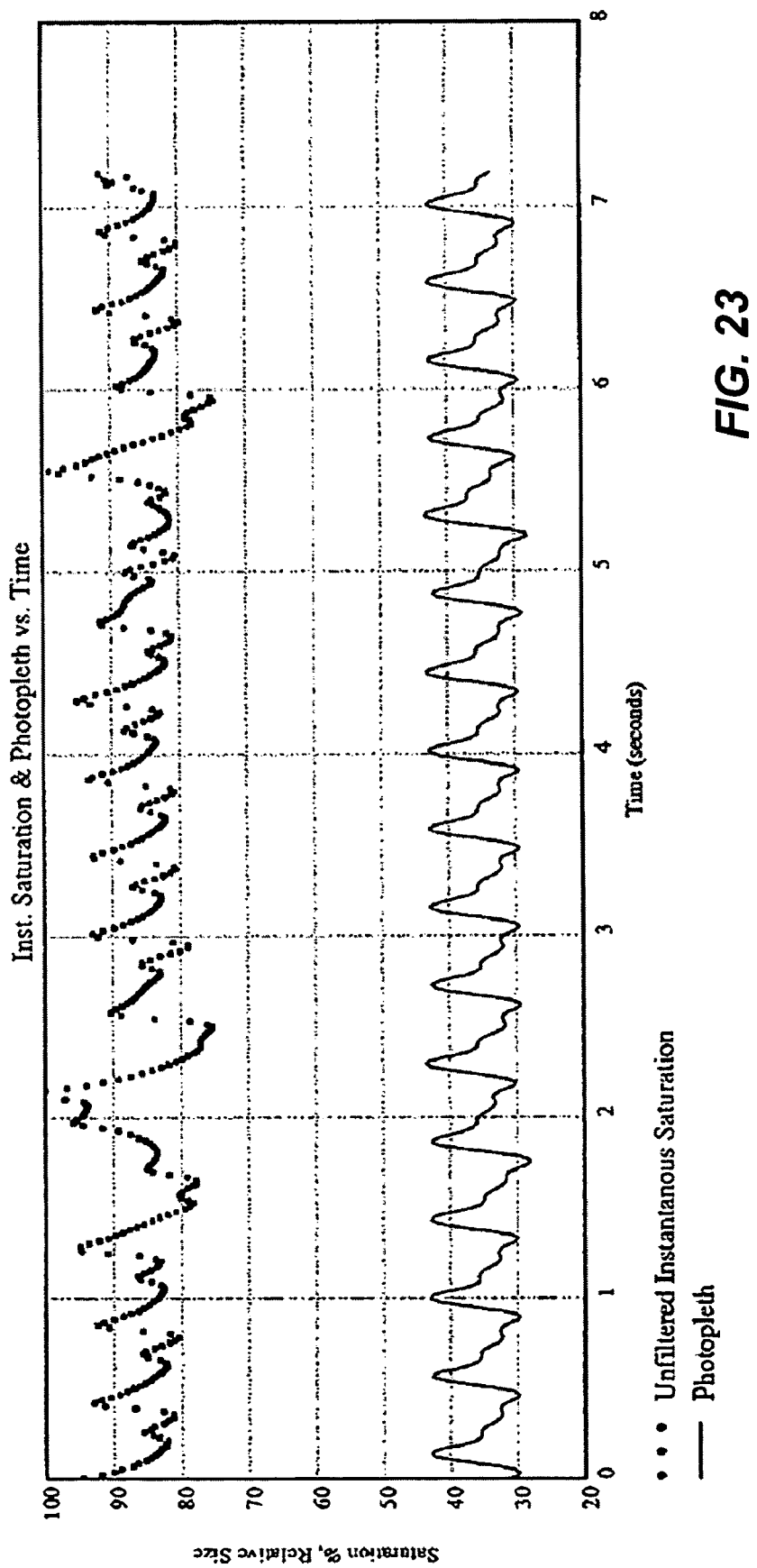
FIG. 23 illustrates an instantaneous saturation which highlights a large spread of values over one photopleth, as compared to that of FIG. 19 and FIG. 20.

Under certain physiological conditions, venous blood in the vascular bed may undergo pulsation that may or may not be coupled to the arterial pulsation. These pulsation can be strong enough as to disrupt the normal ratio calculations thus giving erroneous saturation readings. When the arterial pulsation has a distinct frequency from the venous pulsation, then the arterial pulsation can be isolated using frequency analysis such as the Fast Fourier Transform used to perform a Saturation Transform, as disclosed in U.S. Pat. No. 6,157,850, mentioned in the foregoing. Strong venous coupling may not be necessarily uniform in time across each arterial pulse, and under certain patient conditions the venous pulse may affect only a portion on the photopleth. This can be advantageous for an algorithm that analyzes the information in the time domain. FIGS. 21 and 22 depict Infrared and Red photopleths that are modulated by venous pulsation. Although their shape may look like a normal photopleth, the instantaneous saturation vs. time curve in FIG. 23 illustrates a large spread in the instantaneous saturation values over one photopleth, as compared to that of FIG. 19 and FIG. 20.

Figure 24:
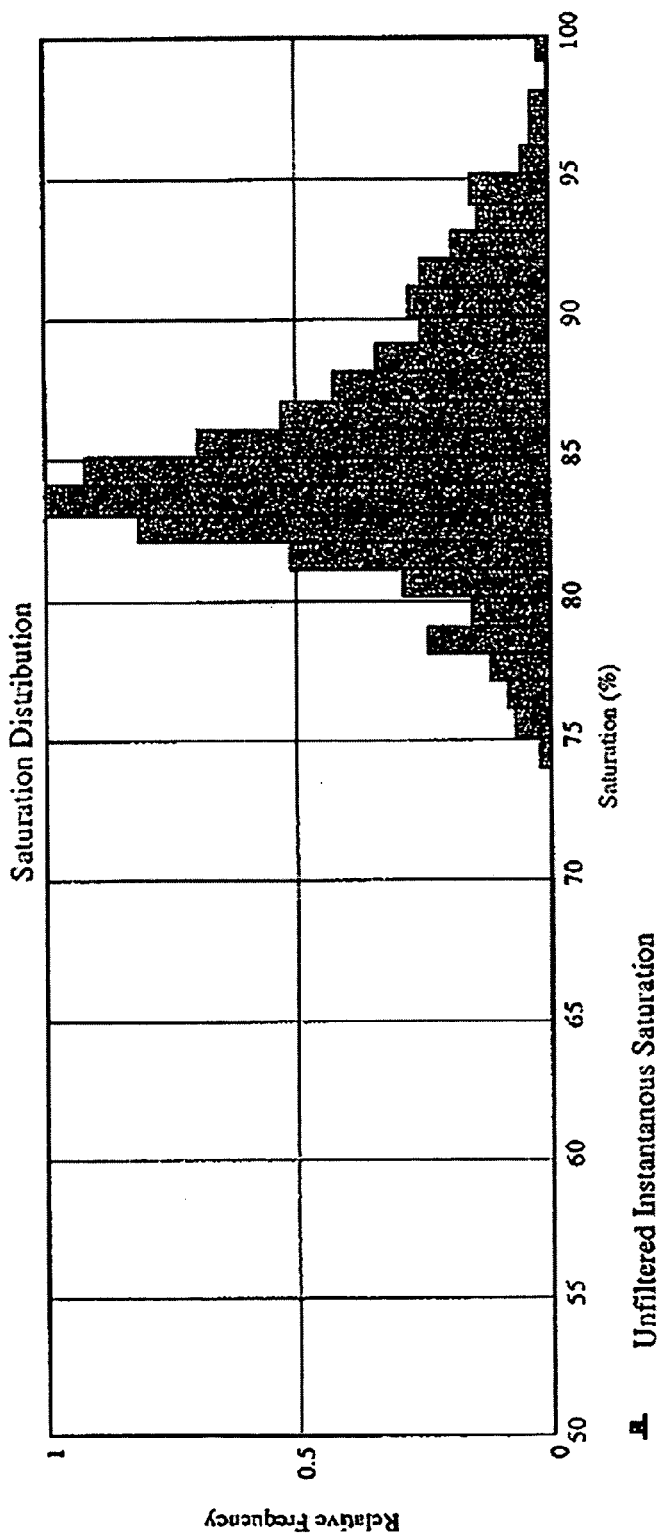
FIG. 24 illustrates a histogram of the distribution of the instantaneous saturation values of FIG. 23.

Under such conditions, taking the average value (or determining the area) of all the instantaneous saturation points may not be the best estimate of the true saturation value. For example, the distribution of the instantaneous saturation values of FIG. 23, e.g. the histogram illustrated in FIG. 24 shows a skewed distribution with a mode at about 83.5 percent (%). This is about 1.8 percent (%) below the average saturation value of about 85.3 percent (%). Another possibility is to phase filter the data and the use the distribution in a similar manner. Phase filtering will be discussed in more detail in the section on managing motion artifacts. In yet another approach, averaging the saturation values over a certain subsection of the photopleth, away from the location of the venous pulsation, can generate more accurate saturation values.

Managing Motion Artifacts

In the context of pulse oximetry, "motion artifacts" refer to any extraneous disturbing source that affects the shape or quality of the optically detected photopleth signal. The disturbance may be a deformation of the vascular bed, a decoupling of the photo detector from the skin, the movement of the sensor itself along the skin surface, or the like. The wide dynamic range of the effect, in terms of its frequency and size, as well as its multiple sources, makes the impact of motion artifacts on the photopleth quite dramatic. More importantly, the impact of motion artifacts on the calculated saturation values can also be very large, thus causing drawbacks in many older generations of pulse oximeters. For example, when motion is repetitive and affects the photopleth over its entirety, then a combination of adaptive filtering and frequency-domain techniques can provide the best estimates of the saturation values. On the other hand, when motion is intermittent or non-repetitive, e.g. pseudo random, then a combination of a time-domain analysis and adaptive filtering techniques with fast adaptation rates works better. While each of the foregoing techniques has its strength and weaknesses, use of multiple parallel engines executing two or more of the foregoing techniques in parallel, and then fusing their results together, often provides best overall performance. Toward that end, the present technique of complex analysis can be a valuable addition to a set of parallel engines that advantageously improves the accuracy of pulse oximeters by correcting for a subset of conditions where the previous algorithms have failed. For example, the ability of the present algorithm to explicitly encode the phase of the signal on a point by point basis renders it very valuable in case of sensor decoupling from the skin where phase decorrelation between Red and Infrared photopleths is prevalent.

Figure 25:
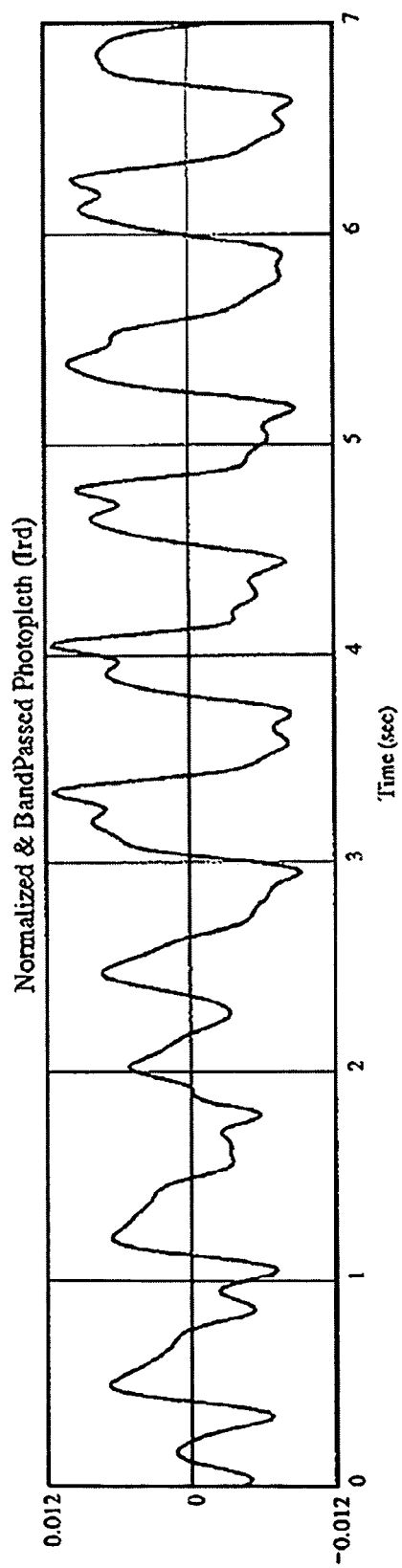
FIGS. 25 and 26 illustrate photopleth signals that are corrupted by motion artifacts.
Figure 26:
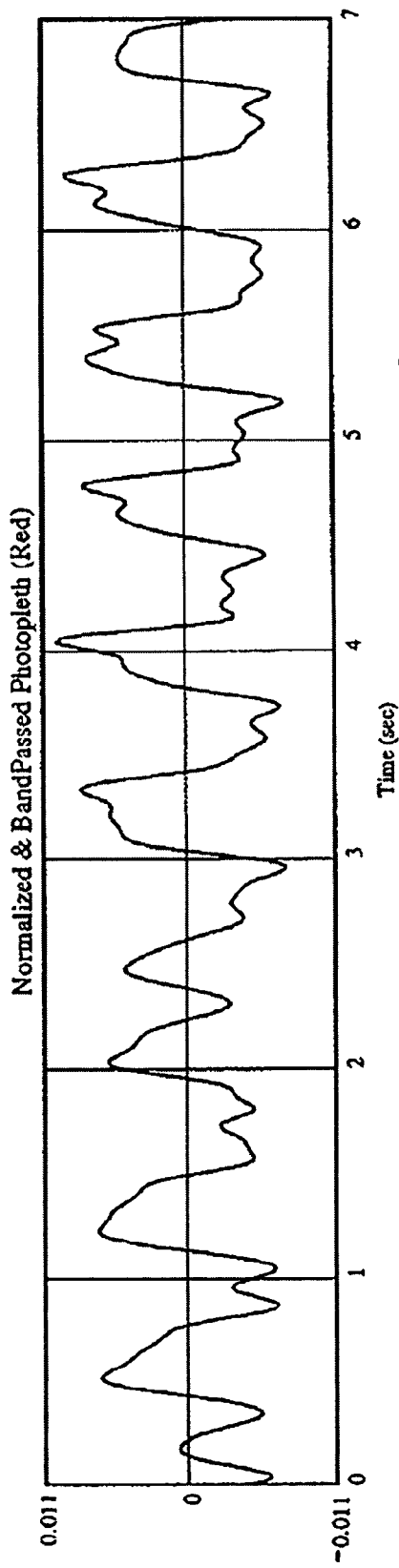
Figure 28:
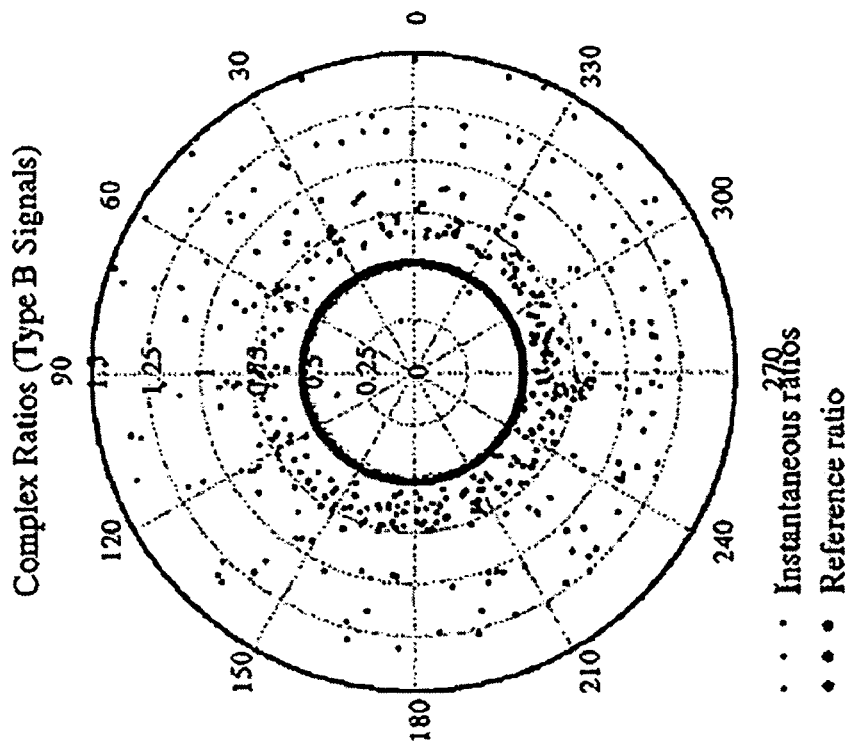
FIG. 28 illustrates a polar plot for type B complex waveforms generated using the photopleths of FIGS. 25 and 26.
Figure 27:
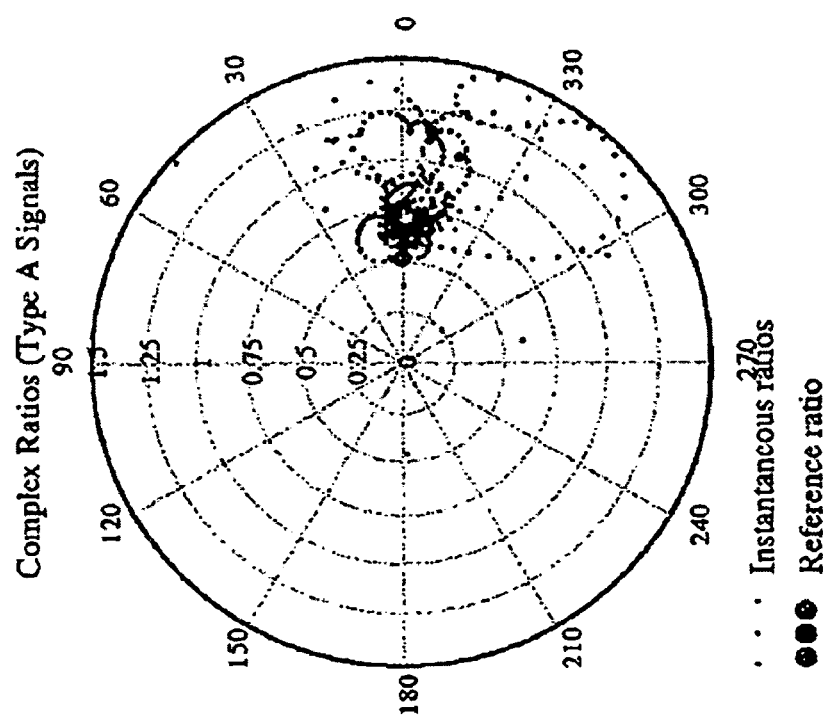
FIG. 27 illustrates a polar plot for type A complex waveforms generated using the photopleths of FIGS. 25 and 26.
Figure 29:
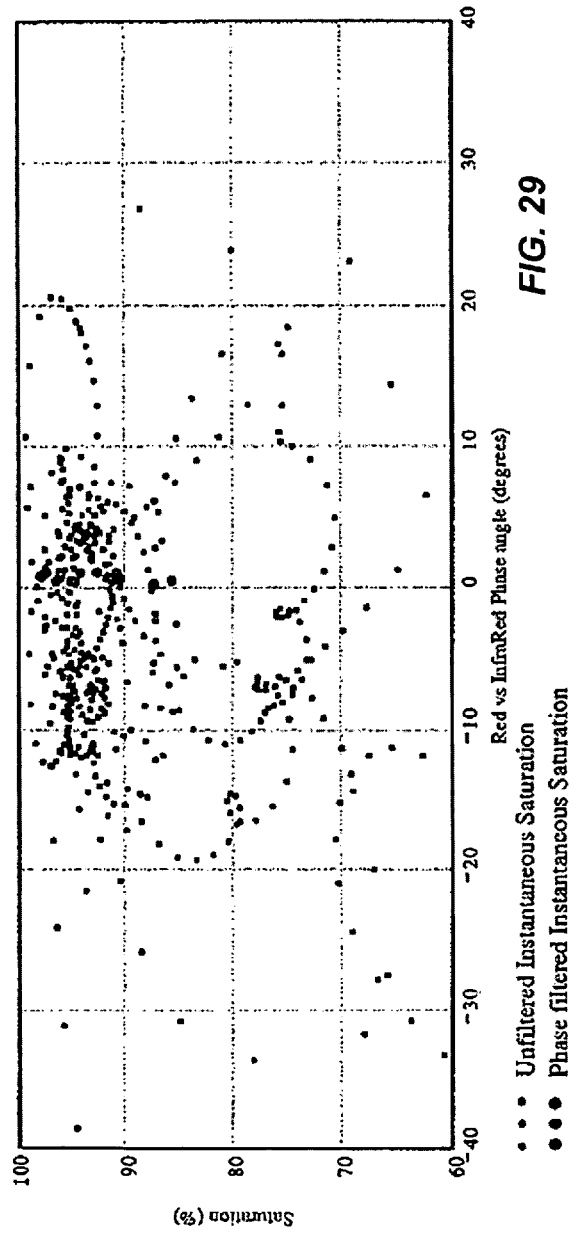
FIG. 29 illustrates the complex ratios of FIG. 27 after being filtered, according to embodiments of the invention.

FIGS. 25 and 26 illustrate photopleth signals that are corrupted by motion artifacts. FIG. 27 illustrates a polar plot for type A complex waveforms generated using the photopleths of FIGS. 25 and 26, while and FIG. 28 illustrates a polar plot for type B complex waveforms generated using the photopleths of FIGS. 25 and 26. It is noteworthy to compare and contrast FIG. 12 with FIG. 27. As disclosed in the foregoing, FIG. 12 illustrates complex ratios where the input signals are motion artifact free. FIG. 12 exhibits a localized point with a magnitude of about 0.53, which generally corresponds to a saturation of about 99 percent (%). Note that the small angle it subtends near the real axis. On the other hand, FIG. 27 illustrates complex ratios where the input signals are riddled with motion artifacts, resulting in ratios with varying magnitudes having widely varying angles.

Figure 30:
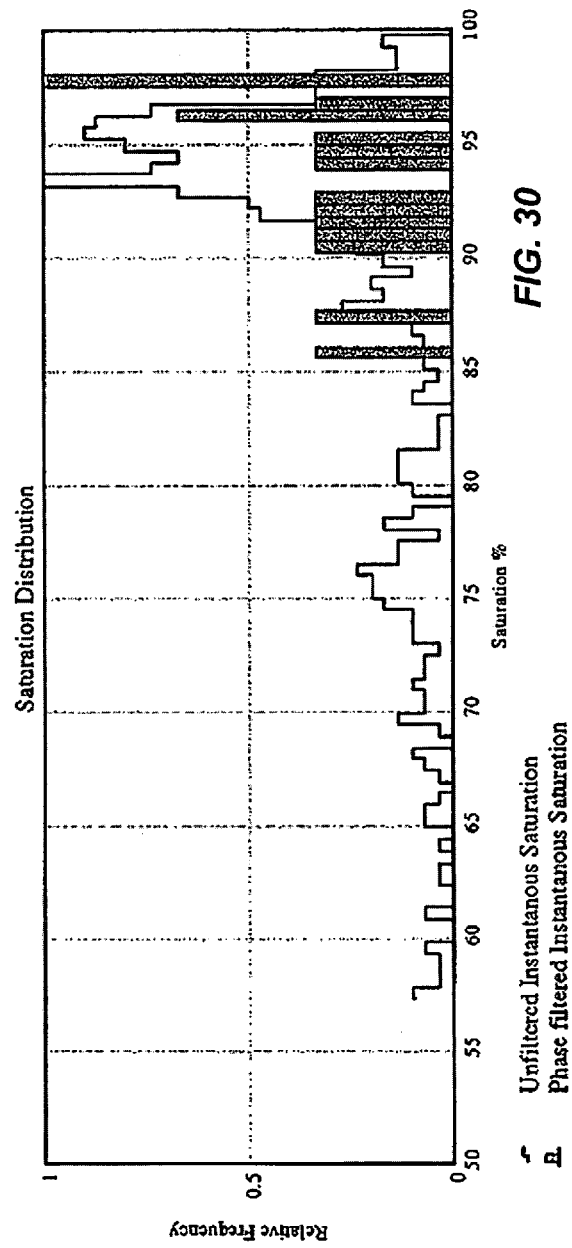
FIG. 30 illustrates a histogram of the filtered saturation points of FIG. 29.
Figure 31:
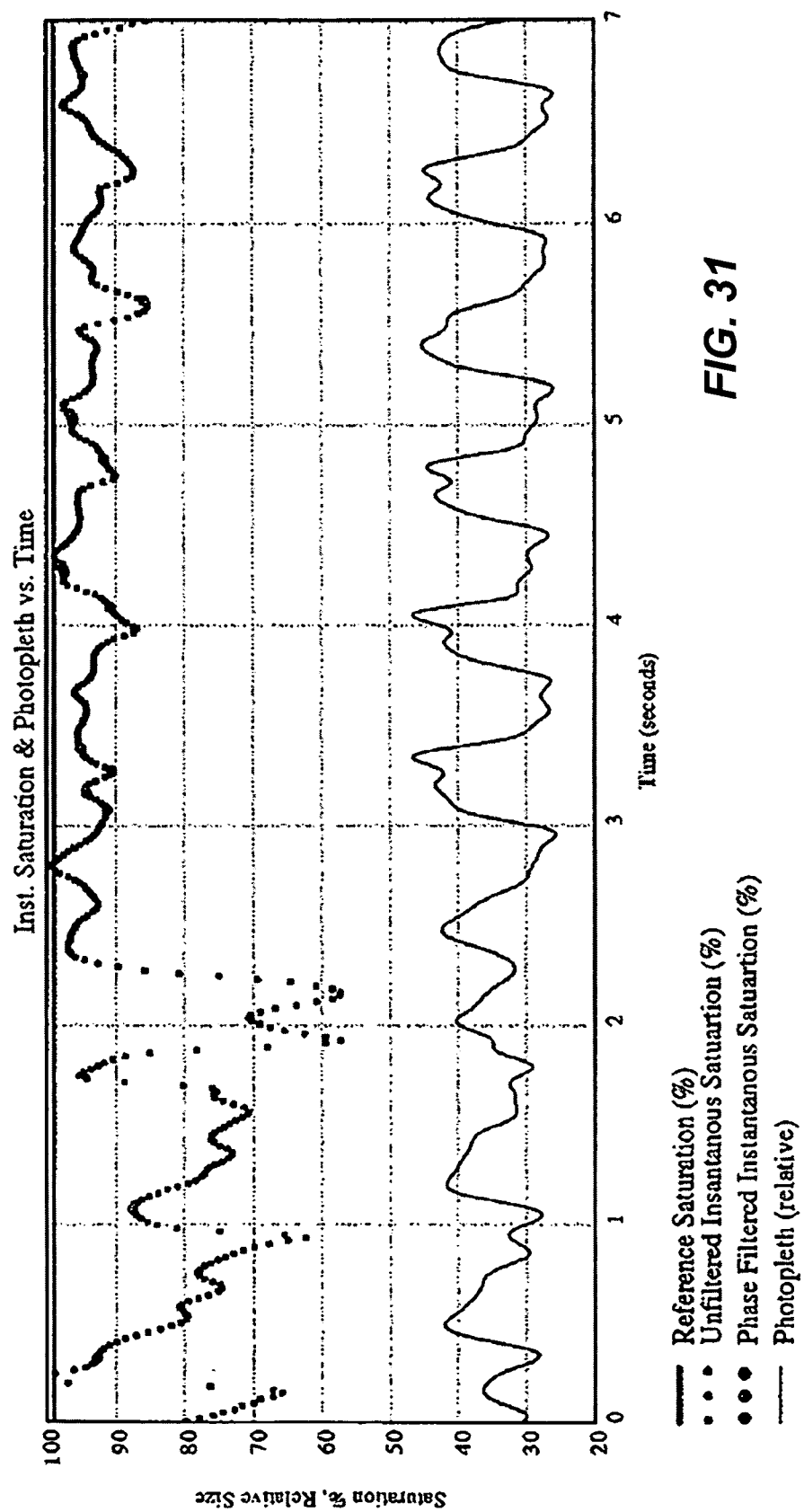
FIG. 31 illustrates plots of unfiltered instantaneous saturation values generated from the photopleths of FIGS. 25 and 26, as well as the phase filtered saturation values of FIGS. 29 and 30.

At the outset, it is difficult to tell which ratios of FIG. 27 are true and which ratios were affected by noise and are therefore, false. However, as shown in FIG. 28, a phase filter can select or pass values similar to those expected, such as, for example, values that subtend low angles from the origin. In one embodiment, the phase filter passes values corresponding to the type and value of phase angles determined, for example, through calibration processes performed and associated with valid data. In an embodiment, the phase filter selects or passes values corresponding to phase angles ranging from about −2.0 to about 3.0 degrees, and more preferably, selects values corresponding to phase angles ranging from about 0.0 to about 1.0 degrees. When the phase filtered saturation points are histogramed, as shown in FIG. 30, the most likely saturation is somewhere near about 98 percent (%), which is only about 1 percent (%) away from the true saturation value of about 99 percent (%). FIG. 31 also includes plots of unfiltered instantaneous saturation values vs. time as well as the phase filtered saturation values plotted on top of them. The corresponding photopleth is also shown for comparison.

Using Frequency Domain Complex Ratios

When a real signal is transformed into the frequency domain, using the Fourier transform for example, the corresponding frequency representation is a series of complex numbers. These complex numbers denote complex frequencies each having a magnitude and a phase. When the Red and Infrared photopleths are transformed into the frequency domain, their corresponding complex frequencies can advantageously be divided to generate complex ratios. Each complex ratio posses a magnitude and a phase similar to the complex ratios generated in the time domain, as disclosed in the foregoing. The frequency domain complex ratios are a representation that has complex ratios vs. frequency, as opposed to representations that have time domain complex ratios vs. time. As disclosed, each technique has its advantages and disadvantages depending on the type of signals present and the nature of the perturbations.

Figure 34:
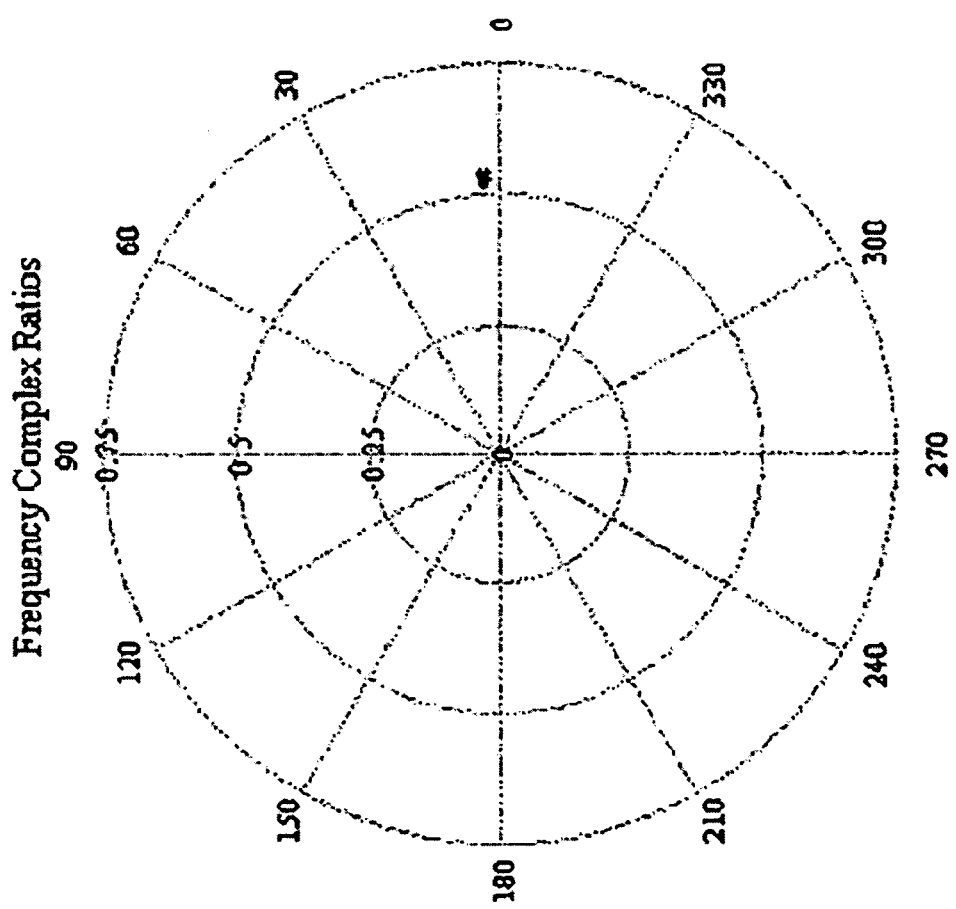
FIG. 34 illustrates the polar plot of the complex frequency ratios of FIG. 32 and FIG. 33.

An example of the use of frequency domain complex ratios according to aspects of the present invention are illustrated in FIG. 32 and FIG. 33. A series of ratios are calculated for the fundamental and first two (2) harmonics of the photopleths waveforms shown in FIG. 2. FIG. 32 illustrates the magnitudes of the complex frequency ratios calculated from the fundamental and harmonics of the photopleths of FIG. 2, while FIG. 33 illustrates frequency transformed photopleths and the phases of the corresponding ratios. FIG. 34 illustrates the polar plot of the complex frequency ratios of FIG. 32 and FIG. 33.

Although the foregoing disclosure generally references various signal processing mechanisms, a skilled artisan will recognize from the disclosure herein that the generators 500, 800, 1100, and 1500 can be implemented with software, firmware, or the like executing on hardware, such as, for example a digital signal processor (DSP). Moreover, the calculations incorporated into the generators can be carried out using software, hardware, or combinations of the same. In addition, the DSP can be part of a portable or stationary device, such as an oximeter, personal monitoring device, or the like.

Although the foregoing invention has been described in terms of certain preferred embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A digital signal processing device which determines one or more physiological parameters of a patient, the digital signal processing device comprising:
   an input configured to accept first data corresponding to a first optical signal attenuated by tissue of a patient and to accept second data corresponding to a second optical signal attenuated by tissue of a patient;
   a first generator configured to transform the first signal into a first modified signal which includes only non-zero values;
   a second generator configured to transform the second signal into a second modified signal which includes only non-zero values;
   a divider which determines ratios of the first modified signal to the second modified signal; and
   a calculator which uses one or more calibration curves and the ratios to determine output values of one or more physiological parameters of the patient.

2. The digital signal processing device of claim 1, wherein the device comprises a pulse oximeter.

3. The digital signal processing device of claim 1, wherein the transform comprises a Hilbert Transform.

4. The digital signal processing device of claim 1, wherein the first modified signal comprises a first complex signal.

5. The digital signal processing device of claim 4, wherein the first complex signal comprises a complex photopleth.

6. The digital signal processing device of claim 1, wherein the device provides point-by-point values for the physiological parameters of the patient.

7. The digital signal processing device of claim 1, further comprising a phase filter configured to pass values of the ratios corresponding to a predetermined range of phases.

8. The digital signal processing device of claim 1, further comprising:
   a correlation generator configured to determine a correlation value between the first modified signal and the second modified signal; and
   a correlation filter configured to pass values of the ratios corresponding to a predetermined set of correlation values.

9. The digital signal processing device of claim 1, further comprising other engines configured to determine other output ratios through processing of the first signal and the second signal, wherein the digital signal processing device selects one of the ratios and other output ratios.

10. The digital signal processing device of claim 1, further comprising other engines configured to determine other output values for the predetermined parameter through processing of the first signal and the second signal, wherein the digital signal processing device selects one of the output values and the other output values.

11. A method of determining a measure of a patient's blood oxygen saturation, the method comprising:
   receiving data corresponding to a plurality of photoplethysmographs;
   encoding each of the plurality of photoplethysmographs as a complex signal;
   combining the plurality of complex signals into complex numbers; and
   determining values of a measure a patient's blood oxygen saturation from the complex numbers.

12. The method of claim 11, further comprising determining a measurement of confidence for each value of the complex numbers.

13. The method of claim 12, further comprising filtering the complex numbers based on the measurement of confidence.

14. The method of claim 12, wherein the measurement of confidence comprises a correlation value.

15. The method of claim 12, wherein the measurement of confidence comprises a value of an associated phase.

16. The method of claim 11, further comprising applying statistical analysis to the complex numbers.

17. A method of processing signals representative of a photodetector output, wherein the photodetector output is indicative of light attenuated by body tissue carrying pulsing blood, the processing performed to assist in a determination of a characteristic of said body tissue, the method comprising:
   receiving data from at least one signal from a photodetector, said at least one signal being indicative of light attenuated by body tissue carrying pulsing blood;
   storing values of said data in the real domain;
   converting said real domain values of said data for each of said at least one signal to separate signals in the complex domain;
   processing said values in the complex domain; and
   determining a characteristic of said body tissue.

* * * * *

UNITED STATES PATENT AND TRADEMARK OFFICE
CERTIFICATE OF CORRECTION

| | | |
|---|---|---|
| PATENT NO. | : 6,970,792 B1 | Page 1 of 2 |
| APPLICATION NO. | : 10/727348 | |
| DATED | : November 29, 2005 | |
| INVENTOR(S) | : Diab | |

It is certified that error appears in the above-identified patent and that said Letters Patent is hereby corrected as shown below:

On Title Page column 1(Assignee) item 73, line 1, delete "Irvine, CA" and insert -- 40 Parker, Irvine, CA 92618 --, therefore.

Sheet 13 of 22, FIG. 20, after "Mean" delete "Satuartion" and insert -- Saturation --, therefore.

Sheet 15 of 22, FIG. 23, delete "Instantanous" and insert -- Instantaneous --, therefore.

Sheet 16 of 22, FIG. 24, after "Unfiltered" delete "Instantanous" and insert -- Instantaneous --, therefore.

Sheet 16 of 22, FIG. 24, after "Mean" delete "Satuartion" and insert -- Saturation --, therefore.

Sheet 19 of 22, FIG. 30, after "Unfiltered" delete "Instantanous" and insert -- Instantaneous --, therefore.

Sheet 19 of 22, FIG. 30, after "filtered" delete "Instantanous" and insert -- Instantaneous --, therefore.

Sheet 20 of 22, FIG. 31, after "Unfiltered" delete "Instantanous Satuartion" and insert -- Instantaneous Saturation --, therefore.

Sheet 20 of 22, FIG. 31, after "Filtered" delete "Instantanous Satuartion" and insert -- Instantaneous Saturation --, therefore.

Sheet 21 of 22, FIG. 32, before "(BPM)" delete "Frequeny" and insert -- Frequency --, therefore.

UNITED STATES PATENT AND TRADEMARK OFFICE
CERTIFICATE OF CORRECTION

PATENT NO. : 6,970,792 B1
APPLICATION NO. : 10/727348
DATED : November 29, 2005
INVENTOR(S) : Diab It is certified that error appears in the above-identified patent and that said Letters Patent is hereby corrected as shown below:

Sheet 21 of 22, FIG. 33, after "Phase" delete "(dgree)" and insert -- (degree) --, therefore.

Sheet 21 of 22, FIG. 33, before "(BPM)" delete "Frequeny" and insert -- Frequency --, therefore.

Signed and Sealed this

Seventeenth Day of July, 2007

JON W. DUDAS
*Director of the United States Patent and Trademark Office*

(12) EX PARTE REEXAMINATION CERTIFICATE (9467th)
United States Patent
Diab

(10) Number: US 6,970,792 C1
(45) Certificate Issued: Jan. 4, 2013

(54) SYSTEMS AND METHODS FOR DETERMINING BLOOD OXYGEN SATURATION VALUES USING COMPLEX NUMBER ENCODING

(75) Inventor: Mohamed K. Diab, Mission Viejo, CA (US)

(73) Assignee: Cercacor Laboratories, Inc., Irvine, CA (US)

Reexamination Request:
No. 90/012,551, Sep. 13, 2012

Reexamination Certificate for:
Patent No.: 6,970,792
Issued: Nov. 29, 2005
Appl. No.: 10/727,348
Filed: Dec. 3, 2003

Certificate of Correction issued Jul. 17, 2007.

Related U.S. Application Data

(60) Provisional application No. 60/430,834, filed on Dec. 4, 2002.

(51) Int. Cl.
*G01N 33/00* (2006.01)
*A61B 5/00* (2006.01)
*A61B 5/04* (2006.01)

(52) U.S. Cl. .................... 702/32; 600/323; 600/515

(58) Field of Classification Search .................. None
See application file for complete search history.

(56) References Cited

To view the complete listing of prior art documents cited during the proceeding for Reexamination Control Number 90/012,551, please refer to the USPTO's public Patent Application Information Retrieval (PAIR) system under the Display References tab.

*Primary Examiner* — Robert Nasser

(57) ABSTRACT

The disclosure includes pulse oximetry systems and methods for determining point-by-point saturation values by encoding photoplethysmographs in the complex domain and processing the complex signals. The systems filter motion artifacts and other noise using a variety of techniques, including statistical analysis such as correlation, or phase filtering.

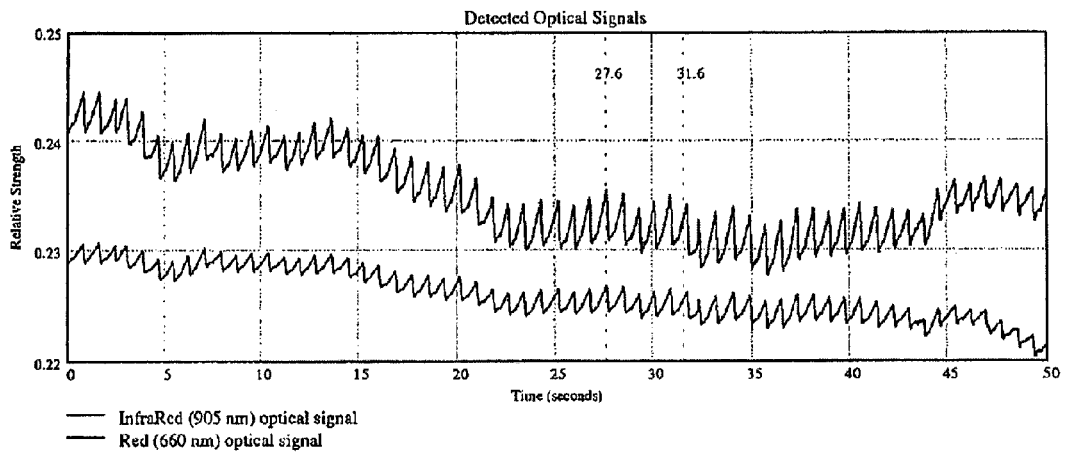

**EX PARTE
REEXAMINATION CERTIFICATE
ISSUED UNDER 35 U.S.C. 307**

NO AMENDMENTS HAVE BEEN MADE TO
THE PATENT

AS A RESULT OF REEXAMINATION, IT HAS BEEN DETERMINED THAT:

The patentability of claims 1-6, 8-14, 16 and 17 is confirmed.

Claims 7 and 15 were not reexamined.

\* \* \* \* \*